(12) United States Patent
Grant et al.

(10) Patent No.: US 7,942,279 B2
(45) Date of Patent: May 17, 2011

(54) DEVICE AND METHOD FOR PACKAGING AND MERCHANDISING PERSONAL HEALTHCARE PRODUCTS

(75) Inventors: Bradford Grant, Bridgewater, NJ (US); Erin Melcher Beam, Califon, NJ (US); William Doskoczynski, Stewartsville, NJ (US); Ronald Jaketic, East Windsor, NJ (US); Opher Yom-Tov, San Francisco, CA (US); Emily Ma, Mountainview, CA (US); Anthony Pigliacampo, Menlo Park, CA (US); Hans-Christoph Haenlein, San Jose, CA (US); Alan Regala, Mountain View, CA (US); Christine McElhaney, Palo Alto, CA (US); Arvind Gupta, Van Nuys, CA (US); Stephen Kim, San Francisco, CA (US); Shilajeet Banerjee, Belmont, CA (US); Stephen Wahl, San Francisco, CA (US); Larry Cheng, Palo Alto, CA (US); Prateek Lal, Clinton, NJ (US)

(73) Assignee: McNeill-PPC, Inc., Skillman, NJ (US)

( * ) Notice: Subject to any disclaimer, the term of this patent is extended or adjusted under 35 U.S.C. 154(b) by 589 days.

(21) Appl. No.: 11/376,448

(22) Filed: Mar. 15, 2006

(65) Prior Publication Data

US 2006/0231453 A1    Oct. 19, 2006

Related U.S. Application Data

(60) Provisional application No. 60/668,841, filed on Apr. 6, 2005.

(51) Int. Cl.
*B65D 50/04* (2006.01)
*B65D 50/00* (2006.01)

(52) U.S. Cl. .................................. 215/216; 215/217
(58) Field of Classification Search .................. 206/581, 206/823, 806, 477, 478, 482, 756, 570, 277, 206/1.9, 148, 493, 223; 220/23.83, 23.87; 215/216, 219, 201, 217, 218, 221; 222/631, 222/633; 604/300
See application file for complete search history.

(56) References Cited

U.S. PATENT DOCUMENTS

| | | |
|---|---|---|
| 1,950,118 A | 3/1934 | Lifton |
| 3,084,830 A | 4/1963 | Koelsch |
| 3,382,969 A | 5/1968 | Cemiak |
| 3,474,936 A * | 10/1969 | McDonnell ................... 222/211 |
| 3,563,405 A | 2/1971 | Zaremski |
| 3,667,647 A | 6/1972 | Van Daalen |
| 3,750,890 A | 8/1973 | Smith et al. |

(Continued)

FOREIGN PATENT DOCUMENTS

DE            8814319         3/1989

(Continued)

*Primary Examiner* — Steven A. Reynolds
(74) *Attorney, Agent, or Firm* — Karen G. Horowitz

(57) ABSTRACT

The invention provides a device and method for packaging and merchandising personal healthcare products. A first aspect of the invention provides a device for storing health care products, comprising: a plurality of product containers, each product container including: a body; a dispensing portion; and an attachment feature; and a housing including a mating feature adapted to be compatible with the attachment feature of each of the plurality of product containers, wherein connection of the attachment feature of a product container and the mating feature of the housing substantially and non-fixedly secures the product container to the housing.

27 Claims, 19 Drawing Sheets

U.S. PATENT DOCUMENTS

| | | | |
|---|---|---|---|
| 3,777,885 A | 12/1973 | Barteck | |
| 3,904,030 A | 9/1975 | Repp et al. | |
| 3,923,152 A | 12/1975 | Minneman | |
| 3,939,982 A | 2/1976 | Russell | |
| 3,952,906 A | 4/1976 | Georgopulos | |
| 4,034,885 A | 7/1977 | Hunckler et al. | |
| 4,117,945 A * | 10/1978 | Mumford | 215/216 |
| 4,133,445 A | 1/1979 | Mandelbaum | |
| 4,149,646 A | 4/1979 | Julian | |
| 4,195,728 A | 4/1980 | Cardamone | |
| 4,383,618 A * | 5/1983 | Dougherty | 215/216 |
| 4,436,211 A | 3/1984 | Gach | |
| 4,480,762 A | 11/1984 | Thomas | |
| 4,588,097 A * | 5/1986 | Hauser | 215/216 |
| 4,752,013 A | 6/1988 | Miller et al. | |
| 4,752,014 A | 6/1988 | House et al. | |
| 5,022,547 A | 6/1991 | Spangler et al. | |
| 5,038,454 A | 8/1991 | Thornock et al. | |
| 5,125,537 A | 6/1992 | Slapin | |
| 5,131,542 A | 7/1992 | Stenstroem et al. | |
| 5,199,567 A * | 4/1993 | Discko, Jr. | 206/369 |
| 5,305,874 A * | 4/1994 | McLaughlin | 206/37 |
| 5,348,194 A * | 9/1994 | Mascitelli et al. | 222/209 |
| 5,351,818 A | 10/1994 | Daneshvar | |
| 5,449,077 A | 9/1995 | Seidler | |
| 5,644,297 A * | 7/1997 | Masi et al. | 340/573.1 |
| 5,687,863 A * | 11/1997 | Kusz | 215/216 |
| 5,706,963 A | 1/1998 | Gargione | |
| 5,722,546 A * | 3/1998 | Briere | 215/216 |
| 5,727,703 A * | 3/1998 | Fuchs | 215/214 |
| 5,799,790 A | 9/1998 | Ziegert et al. | |
| 5,908,125 A | 6/1999 | Opresco | |
| 5,918,752 A | 7/1999 | Meyer | |
| 6,003,700 A * | 12/1999 | Julian et al. | 215/216 |
| 6,076,679 A | 6/2000 | Ideshita et al. | |
| 6,112,921 A | 9/2000 | Robinson | |
| 6,129,210 A | 10/2000 | Fiore et al. | |
| 6,286,679 B1 | 9/2001 | Dirx et al. | |
| 6,296,130 B1 | 10/2001 | Forsyth et al. | |
| 6,360,744 B1 * | 3/2002 | Myrman et al. | 128/203.15 |
| 6,386,209 B1 * | 5/2002 | Yuhara et al. | 132/294 |
| 6,419,088 B1 | 7/2002 | Barrois et al. | |
| 6,497,542 B1 | 12/2002 | Vermeulen | |
| 6,543,650 B1 | 4/2003 | Sprick et al. | |
| 6,612,450 B1 | 9/2003 | Buono | |
| 6,681,945 B1 * | 1/2004 | Harrold | 215/204 |
| 6,854,613 B2 * | 2/2005 | Biesecker et al. | 215/219 |
| 6,866,164 B2 | 3/2005 | Branson et al. | |
| 2002/0079313 A1 | 6/2002 | Grayson | |
| 2003/0044323 A1 | 3/2003 | Diamond et al. | |
| 2003/0116457 A1 | 6/2003 | Belanger | |
| 2004/0104232 A1 * | 6/2004 | Market et al. | 220/23.88 |
| 2005/0023167 A1 | 2/2005 | Yang | |
| 2005/0175338 A1 | 8/2005 | Ide et al. | |
| 2005/0218031 A1 | 10/2005 | Murphy | |
| 2006/0032867 A1 | 2/2006 | Grant | |
| 2006/0108312 A1 | 5/2006 | Robinson | |
| 2006/0126974 A1 | 6/2006 | Camps | |

FOREIGN PATENT DOCUMENTS

| | | |
|---|---|---|
| FR | 1269738 | 8/1961 |
| FR | 2491877 | 4/1982 |
| GB | 2270898 | 3/1994 |
| JP | 55148558 | 11/1980 |
| JP | 8089575 | 4/1996 |
| JP | 9301425 | 11/1997 |
| JP | 2005343564 | 12/2005 |
| WO | WO 9004546 | 5/1990 |
| WO | WO9719003 | 5/1997 |

* cited by examiner

FIG. 1A
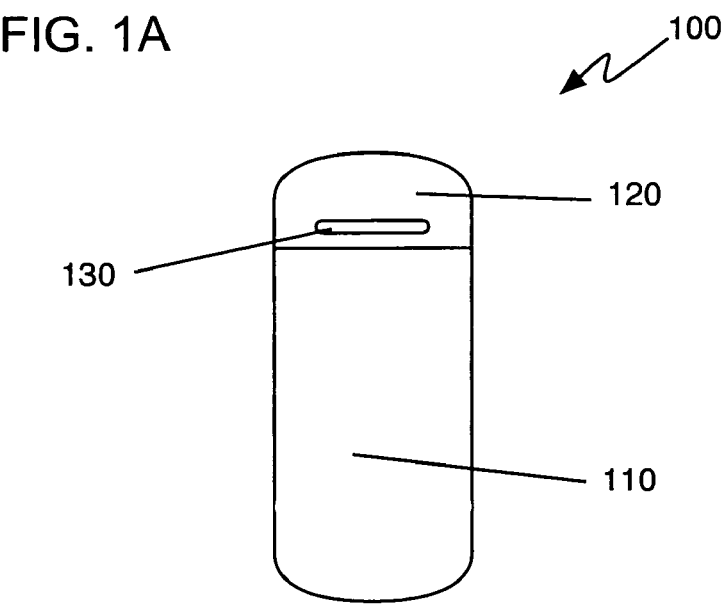
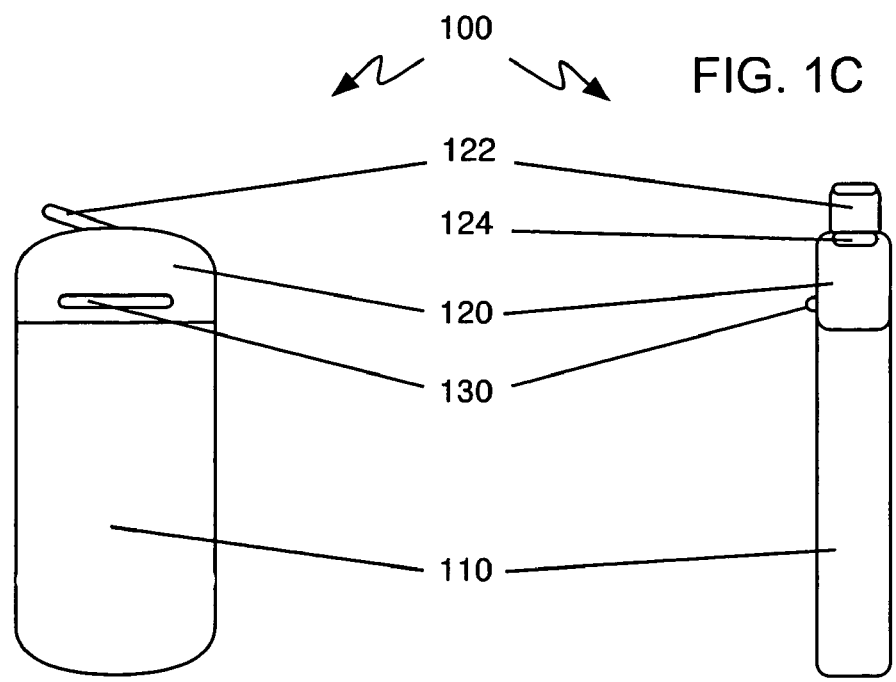
FIG. 1B    FIG. 1C

FIG. 2
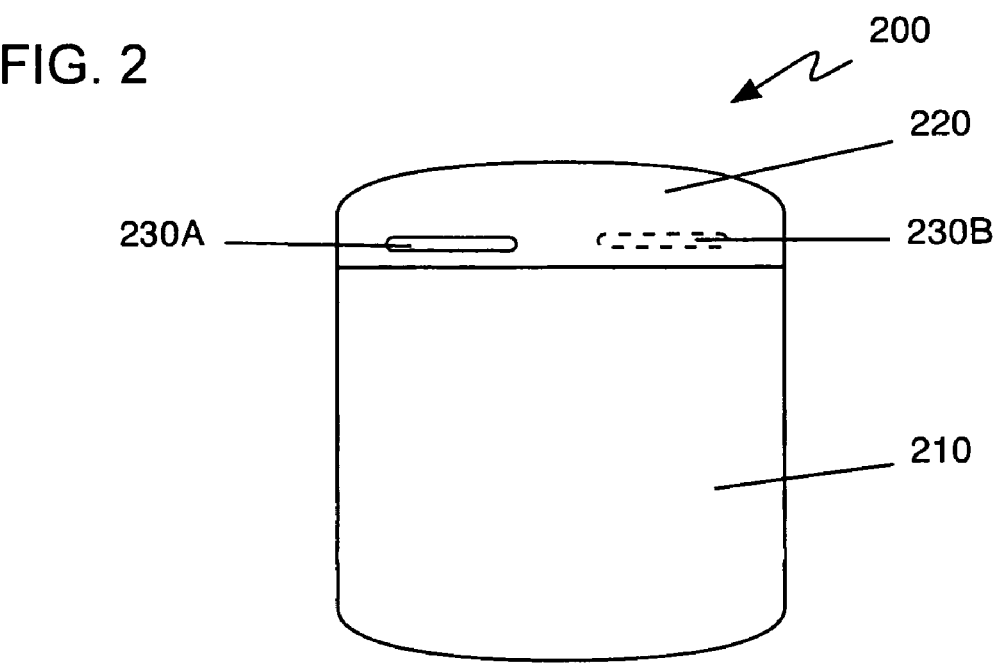
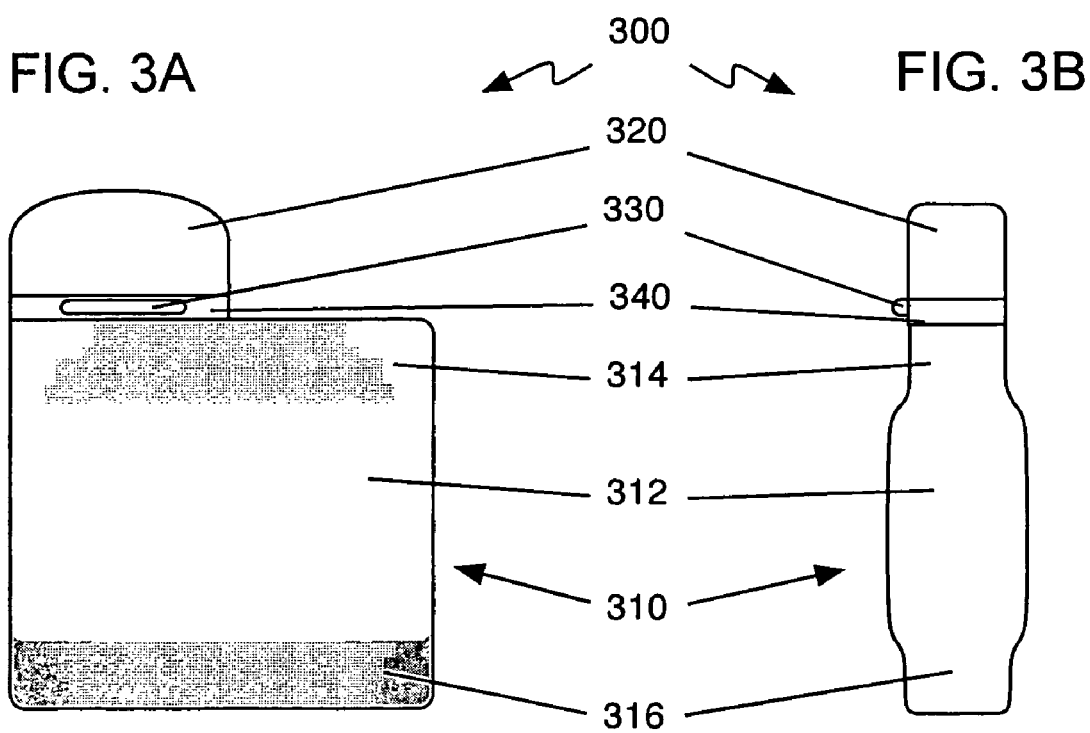
FIG. 3A  FIG. 3B

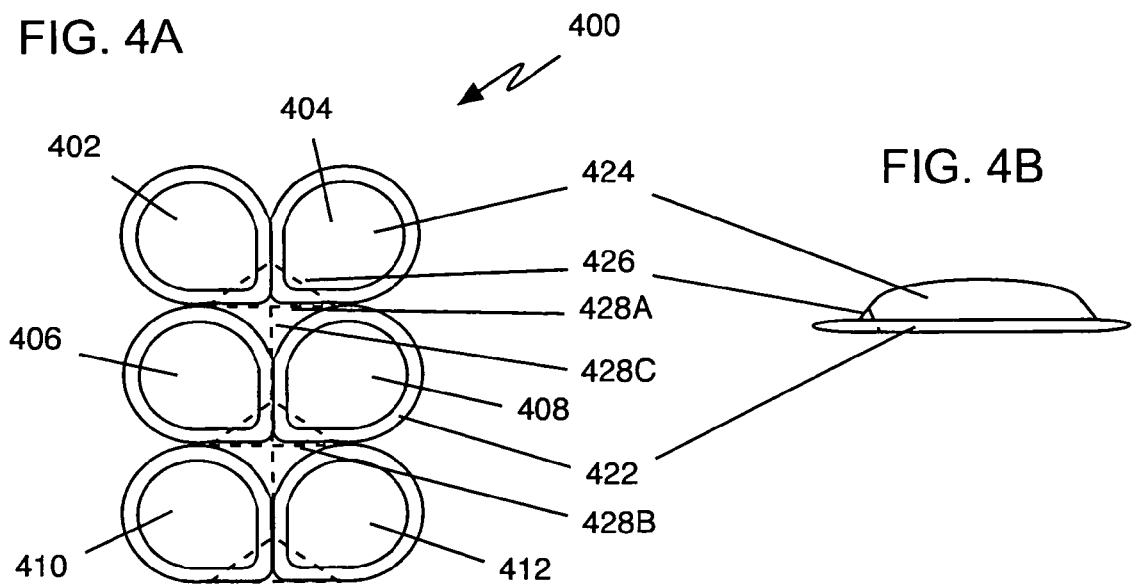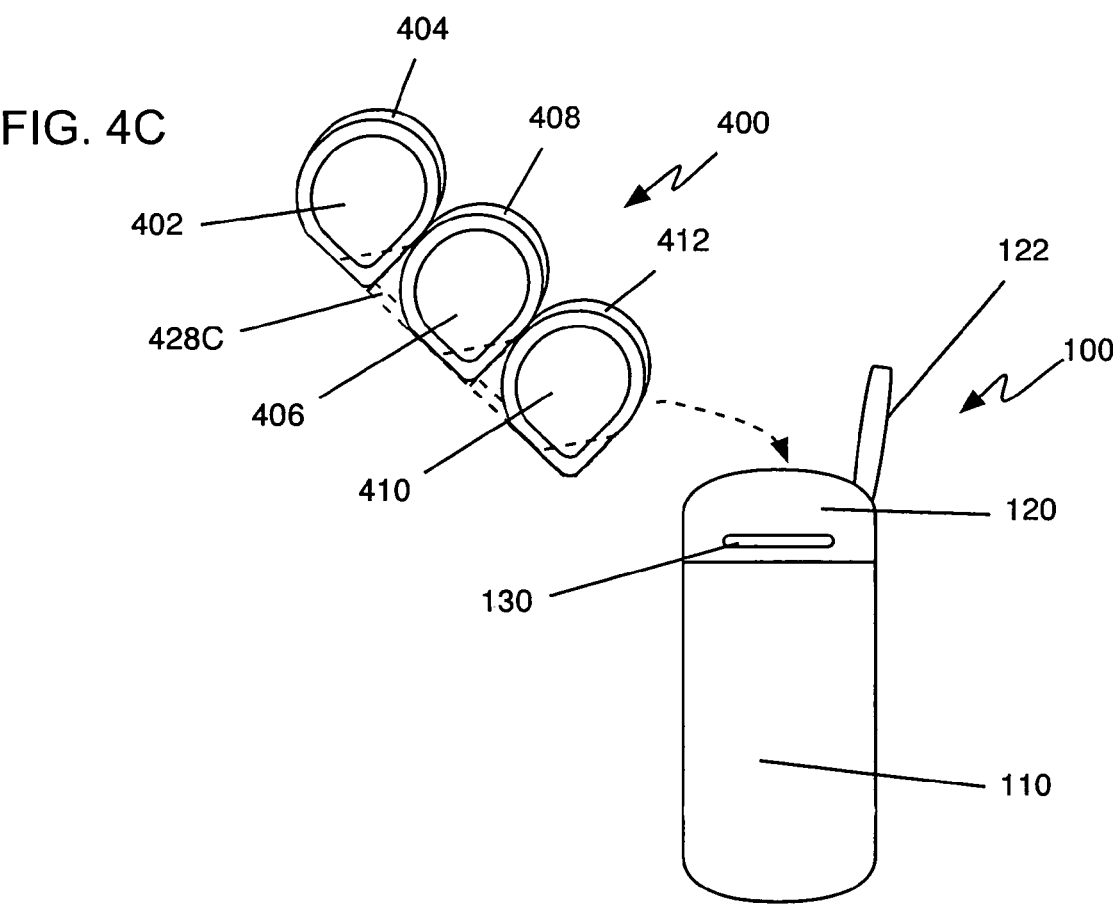

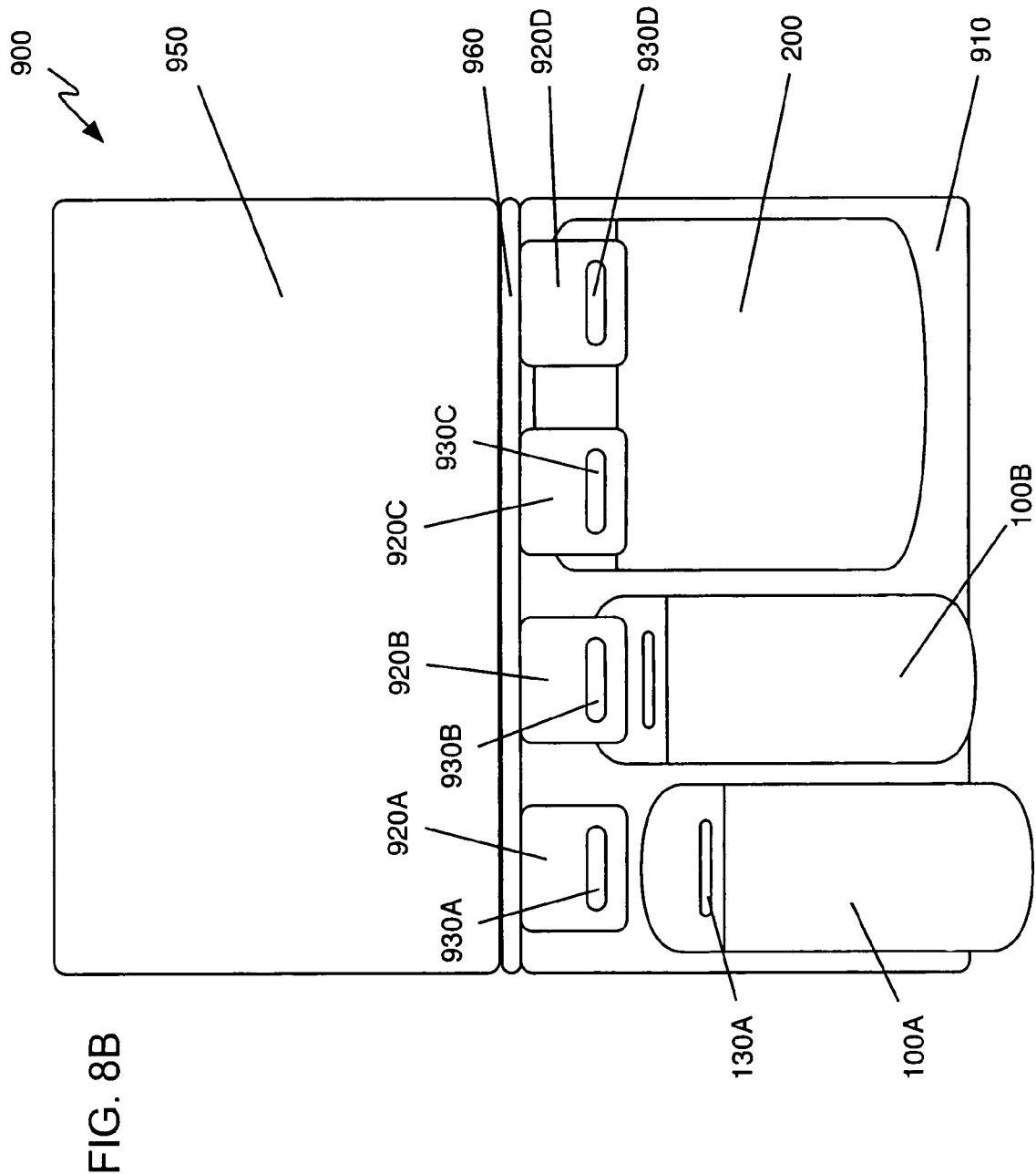

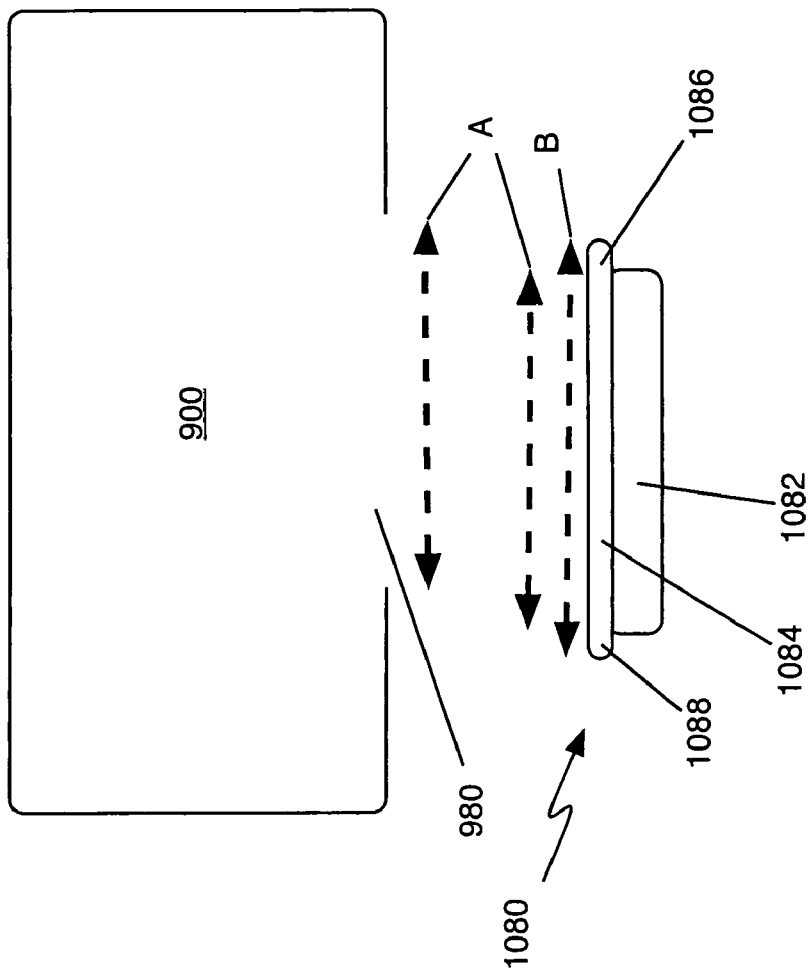
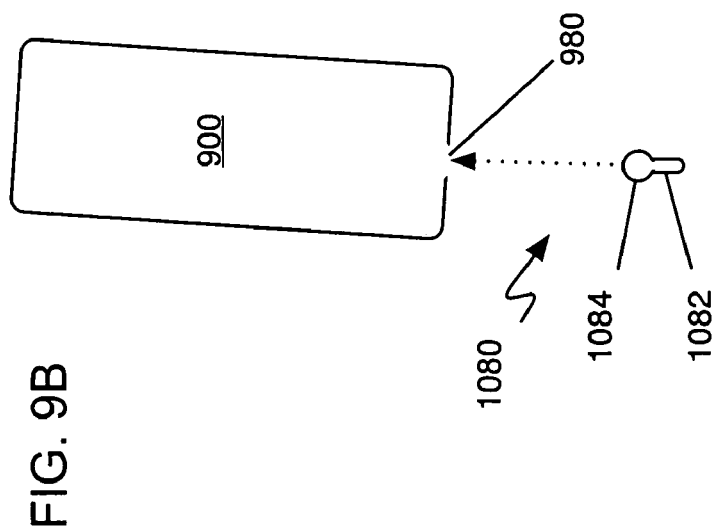

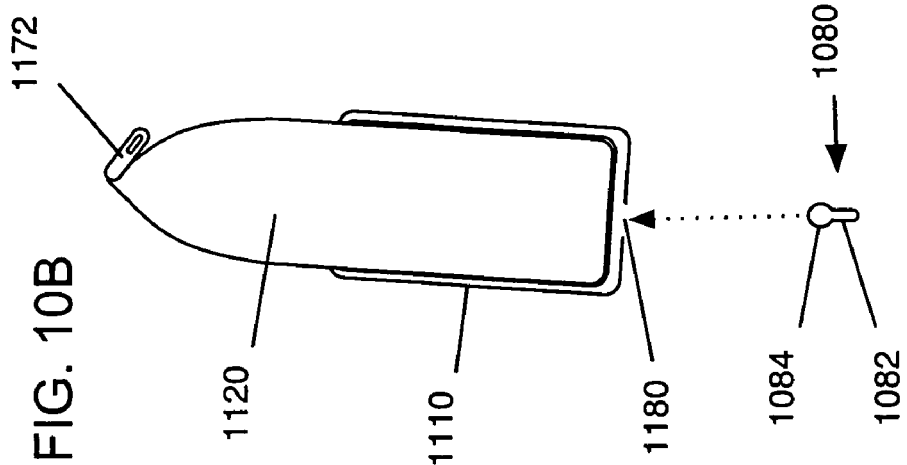
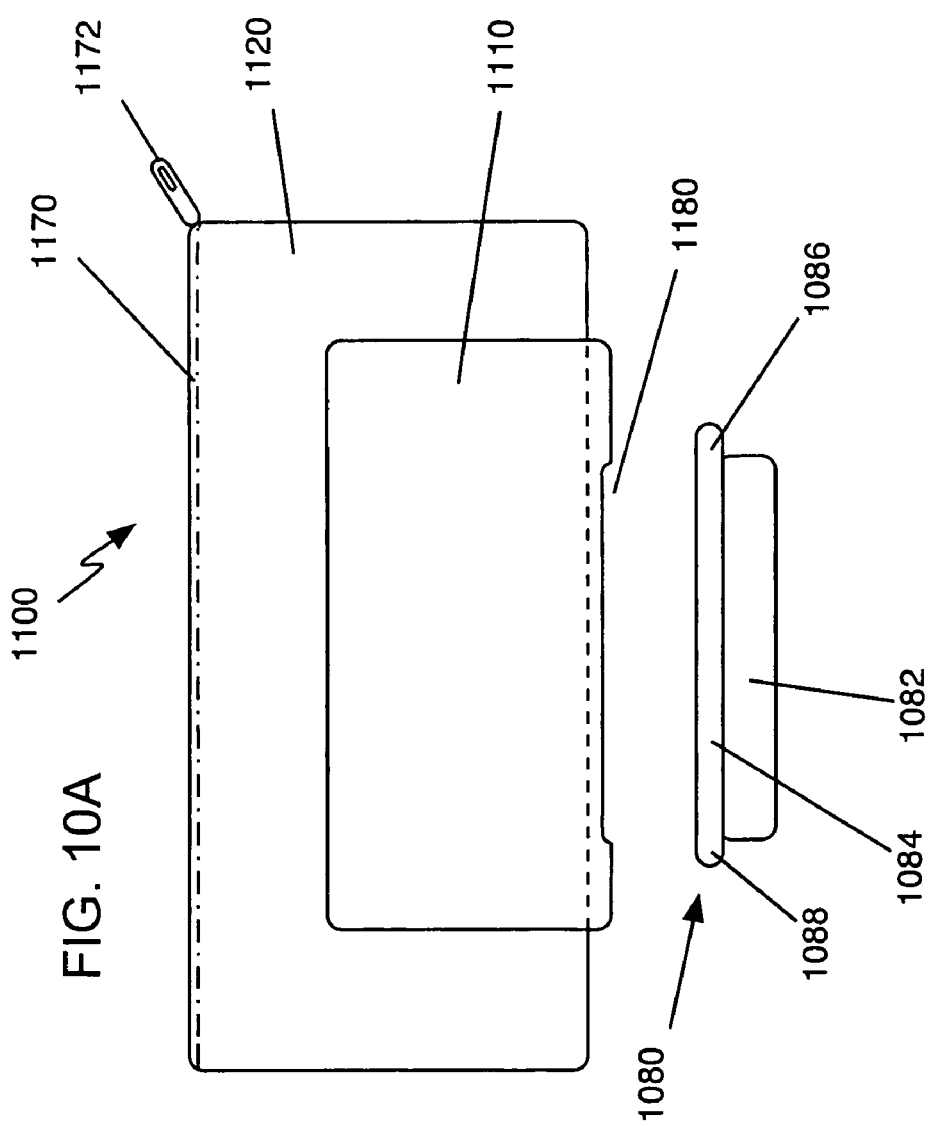

DEVICE AND METHOD FOR PACKAGING AND MERCHANDISING PERSONAL HEALTHCARE PRODUCTS

CROSS REFERENCE TO RELATED APPLICATIONS

The present application claims the benefit of co-pending U.S. Provisional Application No. 60/668,841, filed 6 Apr. 2005, which is hereby incorporated herein.

BACKGROUND OF THE INVENTION

1. Technical Field

The invention relates generally to personal healthcare products, and more particularly, to a system and method for packaging, merchandising, storing, and dispensing personal healthcare products.

2. Background Art

Personal healthcare products encompass a wide variety of products intended to treat and/or alleviate health conditions. Personal healthcare products are typically administered by the individual with the particular health condition to be treated and/or alleviated. Such products may also be administered by a non-healthcare professional, such as a parent or caregiver of an individual with a health condition.

Personal healthcare products include first aid medications intended to treat topical wounds; mouthwashes; tooth and gum analgesics; dental floss; tooth brushes; breath fresheners; breath sprays; treatments for upper respiratory conditions, including decongestants, antihistamines, cough suppressants, and medicaments for allergy, cold, cough, or sinus relief; anti-gas remedies; eye care solutions; antacids; gastrointestinal treatments; anti-itch preparations; bandages; lip care treatments; lotions; motion sickness treatments; anti-diarrheals; analgesics; allergy medications; medicines; sanitizers; wipes; tissues; antibiotic ointments; sprays; topical analgesics; heating patches; hair regrowth compositions; anti-inflammatory treatments; gums (e.g., nicotine-containing, tooth-whitening, etc.); tobacco dependence treatments, etc.

Current systems and methods for packaging, storing, merchandising, dispensing, and using consumer healthcare products are not well suited for users perceived as having a greater need for portable or mobile healthcare. For example, typical merchandising systems, such as those employed in food and drug outlets, separate personal healthcare products according to category or symptom. For example, various brands of products for pain treatment are grouped together on a shelf or in a section while various brands of products for the treatment of upper respiratory ailments are separately grouped together on a different shelf or in a different section.

Such merchandising systems are not ideal for customers perceived as having a greater need for portable or mobile healthcare. Customers with limited time to shop and make choices as to personal healthcare items may find it frustrating to go through all of the shelves, sections, or aisles of a merchandiser to find and/or obtain the products they desire or need. Those with limited time, who are often traveling or otherwise away from home, or those who do not plan in advance for their personal healthcare needs, may find it helpful to have selected or core personal healthcare items provided in a central, localized, and/or defined area.

Others have attempted to provide devices for containing and/or dispensing personal healthcare products for use when traveling. For example, U.S. Pat. No. 5,351,818 to Daneshvar describes a box for housing medicines in separate compartments as an aid in adhering to a dosage regimen. However, the Daneshvar device suffers from a number of defects. First, it is relatively large, making it impractical for use when traveling. Second, it is capable of housing personal healthcare products of only a few, limited forms. Specifically, the Daneshvar device is capable of housing only solid products, such as pills and tablets. Third, personal healthcare products housed in the Daneshvar device still must be purchased in typical packaging (e.g., pill bottles, etc.) and then transferred to the device.

U.S. Patent Application Publication No. 2005/0218031 to Murphy describes interlocking storage units, wherein individual units may be disconnected from a larger group of interlocked units and used, for example, when traveling. However, as with the Daneshvar device discussed above, the Murphy device in incapable of housing many forms of personal healthcare products, such as liquids, gels, and powders. The Murphy device also requires the purchase of personal healthcare products in typical packaging and then the transfer of such products to the device.

To this extent, a need exists for a system and method for packaging, merchandising, storing, and/or dispensing personal healthcare products that do not suffer from the defects of known systems and methods.

SUMMARY OF THE INVENTION

The invention provides a device and method for packaging and merchandising personal healthcare products.

A first aspect of the invention provides a device for storing health care products, comprising: a plurality of product containers, each product container including: a body; a dispensing portion; and an attachment feature; and a housing including a mating feature adapted to be compatible with the attachment feature of each of the plurality of product containers, wherein connection of the attachment feature of a product container and the mating feature of the housing substantially and non-fixedly secures the product container to the housing.

A second aspect of the invention provides a container for storing a healthcare product, the container comprising: a body; a dispensing portion; and an attachment feature, wherein the attachment feature is adapted to be compatible with a mating feature of a housing for substantially securing the container.

A third aspect of the invention provides a housing for substantially securing a plurality of product containers comprising: a base portion; and a plurality of mating features, each mating feature being adapted to be compatible with an attachment feature of a product container.

A fourth aspect of the invention provides a child-resistant dispensing mechanism comprising: a cap portion including: a threaded female member; and at least one deflectable member; and a base portion including: a threaded male member adapted to thread into and out of the threaded female member; and at least one groove adapted to receive at least a portion of the at least one deflectable member, wherein the at least one deflectable member, in a non-deflected state, is located within the at least one groove and substantially prevents the cap portion from being threadably removed from the base portion and, in a deflected state, may be removed from the at least one groove as the cap portion is threadably removed from the base portion.

A fifth aspect of the invention provides a liquid dispensing device comprising: a liquid-containing portion; a mid portion including an aperture; a bulb member adapted to aid a user in forcing a liquid within the liquid-containing portion through the aperture; and a cover portion slidably connected to the mid portion and adapted to alternately cover and reveal the aperture, wherein the cover portion substantially prevents the liquid from being dispensed through the aperture when the cover portion covers the aperture.

A sixth aspect of the invention provides a storage device comprising: a flexible enclosure; a rigid frame for holding the enclosure; and an attachment feature disposed on the frame for substantially securing the storage device to a case.

An seventh aspect of the invention provides a method for merchandising personal healthcare products, the method comprising: providing, in a single area of a merchandiser's establishment, a plurality of personal healthcare products, wherein each of the plurality of personal healthcare products is packaged in a product container adapted to be secured to a housing.

The illustrative aspects of the present invention are designed to solve the problems herein described and other problems not discussed, which are discoverable by a skilled artisan.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which:

FIGS. 1A-C show an illustrative product container according to the invention.

FIG. 2 shows an alternative product container according to the invention.

FIGS. 3A-B show an alternative product container according to the invention.

FIGS. 4A-C show an illustrative product container according to the invention for storing and dispensing individual dosages of a liquid or lotion.

FIGS. 8A-D show an illustrative product container housing according to the invention.

FIGS. 9A-G show various views of cases and attachment mechanisms for storing product container housings according to the invention.

FIGS. 10A-B show an illustrative flexible storage device according to the invention.

It is noted that the drawings of the invention are not to scale. The drawings are intended to depict only typical aspects of the invention, and therefore should not be considered as limiting the scope of the invention. In the drawings, like numbering represents like elements between the drawings.

DETAILED DESCRIPTION

Figure 5A:
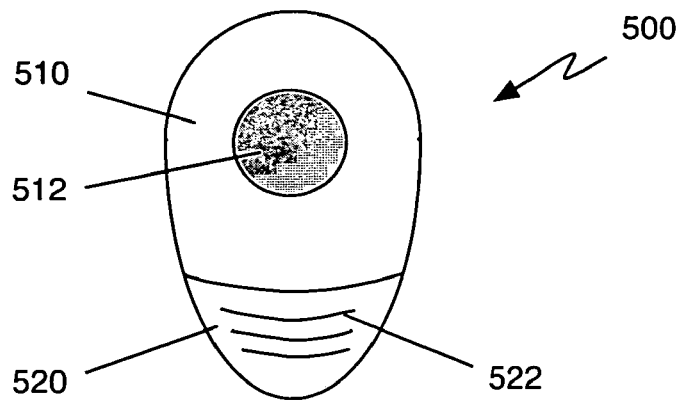
FIGS. 5A-E show illustrative product containers according to the invention for storing and dispensing a liquid.

As indicated above, the invention provides a system and method for packaging, merchandising, storing, and dispensing personal healthcare products.

FIGS. 1A-C show front and side views of an illustrative embodiment of a product container 100 according to the invention. In FIG. 1A, product container 100 includes a body 110, a dispensing portion 120, and an attachment feature 130.

Body 110 may be of any number of materials, depending on the personal healthcare product it is to contain. For example, body 110 may comprise a rigid material, in the case that product container 100 is to contain pills, tablets, capsules, powders, or other healthcare products requiring little or no manipulation of body 110 to dispense. Alternatively, body 110 may comprise a flexible material, in the case that product container 110 is to contain a liquid, gel, or other healthcare product, the dispensation of which may require manipulation (e.g., squeezing) of body 110.

As shown, dispensing portion 120 includes a lid 122 (FIG. 1B) for sealing an opening 124 (FIG. 1C) for dispensing a personal healthcare product from body 110. Devices other than lid 122 may similarly be used, as will be recognized by one having skill in the art. Illustrative devices include, for example, slide mechanisms, push-button mechanisms, shaker mechanisms, screw caps, etc.

Attachment feature 130 is shown as a ridge or protrusion on an exterior surface of dispensing portion 120. As will be explained in greater detail below, attachment feature 130 enables the securing of product container 100 to a mating feature of a housing (not shown). Accordingly, any number of other attachment features may be employed. Illustrative attachment features include, for example, snaps, clasps, magnets, hooks and loops, tongues and grooves, adhesives, etc. While shown on an exterior surface of dispensing portion 120, attachment feature 130 may be located elsewhere on product container 100, such as an exterior surface of body 110.

Finally, while shown as having a generally rectangular shape, product container 100 may be of any number of shapes, as will be recognized by one having skill in the art. Any such shape should not, however, impede the easy transport of the product container, such as in a user's pocket.

Referring now to FIGS. 2 and 3A-B, alternative embodiments of product containers according to the present invention are shown. In FIG. 2, product container 200 is wider than the product container 100 of FIGS. 1A-C. Preferably, each alternative embodiment of product containers according to the present invention is sized to be a multiple of another of the alternative embodiments, an integer of another of the alternative embodiments, or both. For example, product container 200 of FIG. 2 is approximately twice as wide as product container 100 of FIGS. 1A-C. Correspondingly, product container 100 of FIGS. 1A-C is approximately half the width of product container 200 of FIG. 2. Alternatively, alternative embodiments of the product container according to the present invention may be of substantially the same size. As will be explained in greater detail below, either of these arrangements permit the use of any number of alternative embodiments of a product container according to the invention in combination with a housing for securing such product containers.

As in the alternative embodiment of FIGS. 1A-C, product container 200 of FIG. 2 includes a body 210, a dispensing portion 220, and an attachment feature 230A. Where product container 200 is sized to be a multiple of an alternative embodiment, additional attachment features 230B (shown in phantom) may optionally be included, such that each attachment feature 230A, 230B is spaced substantially as though each was located on an integer sized alternative embodiment. For example, attachment features 230A, 230B are spaced relative to each other substantially as though each was located on one of a pair of product containers 100 of FIGS. 1A-C, with each product container 100 positioned adjacent the other.

FIGS. 3A-B show front and side views, respectively, of yet another alternative embodiment of a product container 300 according to the invention. Body 310 of product container 300 comprises a flexible material, such that body 310 may be squeezed or otherwise manipulated to remove its contents. As shown, body 310 includes tapered end portions 314, 316 and a distended center portion 312, although other arrangements are similarly useful.

In the case that body 310 comprises a flexible material and dispensing portion 320 comprises a rigid material, it may be desirable to include a collar 340 between body 310 and dispensing portion 320. Thus, rather than attaching dispensing portion 320 directly to body 310, body 310 may be fixedly attached (e.g., adhesively, thermal sealed, etc.) to collar 340. Dispensing portion 320 may then be fixedly or non-fixedly attached to collar 340. Such an arrangement may be useful in filling body 310 with a personal healthcare product, such as a gel or a lotion, before attachment of dispensing portion 320.

As shown in FIG. 3A, body 310 may be wider than dispensing portion 320. Such an arrangement may be desirable, for example, where body 310 contains a relatively large quantity of a personal healthcare product that requires only a relatively small dispensation mechanism.

FIGS. 4A-C show a dispensing device 400 for the storage and dispensation of single dosages of a personal healthcare product such as a liquid or a lotion. As shown in FIGS. 4A-B, each dispensing device 400 comprises one or more "pods" 402, 404, 406, 408, 410, 412. Preferably, a plurality of pods is provided, with individual pods being connected, as shown in FIG. 4A. Each pod comprises a reservoir 424, a circumference of which is surrounded by a ring 422. In order to facilitate easy removal of the personal healthcare product from reservoir 424, ring 422 and reservoir 424 include a perforation 426. As will be recognized by one having skill in the art, perforation 426 allows a user to tear through ring 422 and open reservoir 424. Once opened, the contents of reservoir 424 may be removed by, for example, squeezing reservoir 424.

Dispensing device 400 includes a number of other perforations 428A, 428B, 428C. Horizontal perforations 428A, 428B allow a user to remove pairs of pods, for example, after they are emptied. In addition, vertical perforation 428C allows a user to remove individual pods, when used in conjunction with a horizontal perforation 428A, 428B.

As shown in FIG. 4C, dispensing device 400 may be stored in a product container 100, such as that of FIGS. 1A-C, by folding dispensing device 400 along vertical perforation 428C. As will be explained below, so storing dispensing device 400 permits its storage and transport within a housing adapted to secure one or more product containers.

Figure 5B:
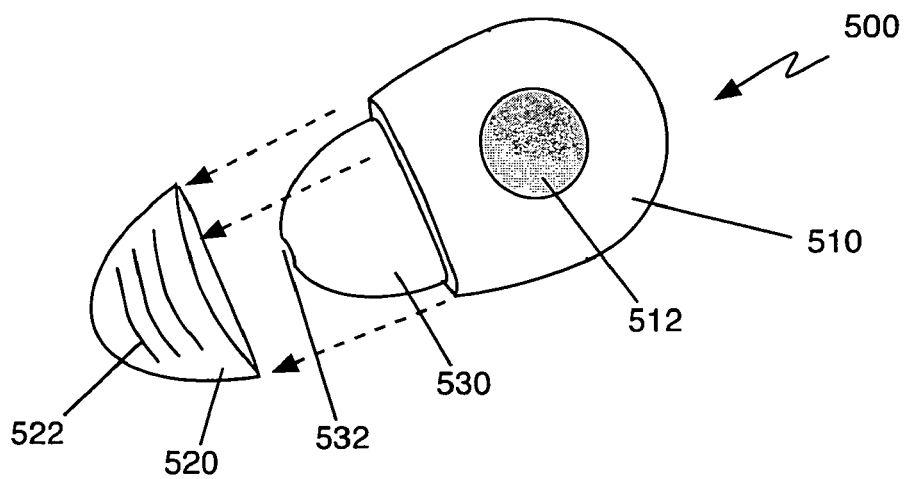

FIGS. 5A-E show various views of alternative embodiments of a liquid dispensing device according to the invention. In FIGS. 5A-B, a first embodiment of a liquid dispensing device 500 is shown, comprising a flexible body 510 for storing a liquid, a mid piece 530 including an aperture 532, a bulb 512 to aid in forcing a liquid within body 510 through the aperture 532, and a cap 520. Bulb 512 is shown as a depression within the surface of body 510, which aids in a user properly positioning his or her finger or thumb when dispensing the liquid. Bulb 512 may similarly comprise a raised portion of the surface of body 510 or may simply comprise a marking on the surface of body 510. As noted above, body 510 is sufficiently flexible that it may be squeezed or otherwise manipulated in order to force a liquid from within body 510 through aperture 532.

As shown in FIGS. 5A-B, cap 520 is removable from the remainder of dispensing device 500. Preferably, cap 520 may be non-fixedly attached to body 510 and/or mid piece 530 via an interference joint, although other mechanisms are also possible, as will be recognized by one skilled in the art. To aid in the removal of cap 520, an exterior surface may include ridges 522 or similar structures to aid in a user's grip of cap 520. When in place, cap 520 preferably substantially prevents the dispensation of a liquid through aperture 532. For example, the mechanism of joining cap 520 to body 510 and/or mid piece 530 is preferably sufficiently airtight that any squeezing of bulb 512 when cap 520 is in place will result in a buildup of pressure within cap 520 sufficient to prevent the dispensation of liquid from body 510. Other mechanisms for preventing the dispensation of liquid are possible, such as a plug (not shown) on an interior surface of cap 520 adapted to fit within aperture 532 when cap 520 is in place.

Dispensing device 500 may be employed to store and dispense any personal healthcare product having a relatively low viscosity, such that the product is dispensed substantially in the form of drops or a stream. Eyedrops and saline solutions are particularly well suited for storage in and dispensation by dispensing mechanism 500.

Figure 5C:
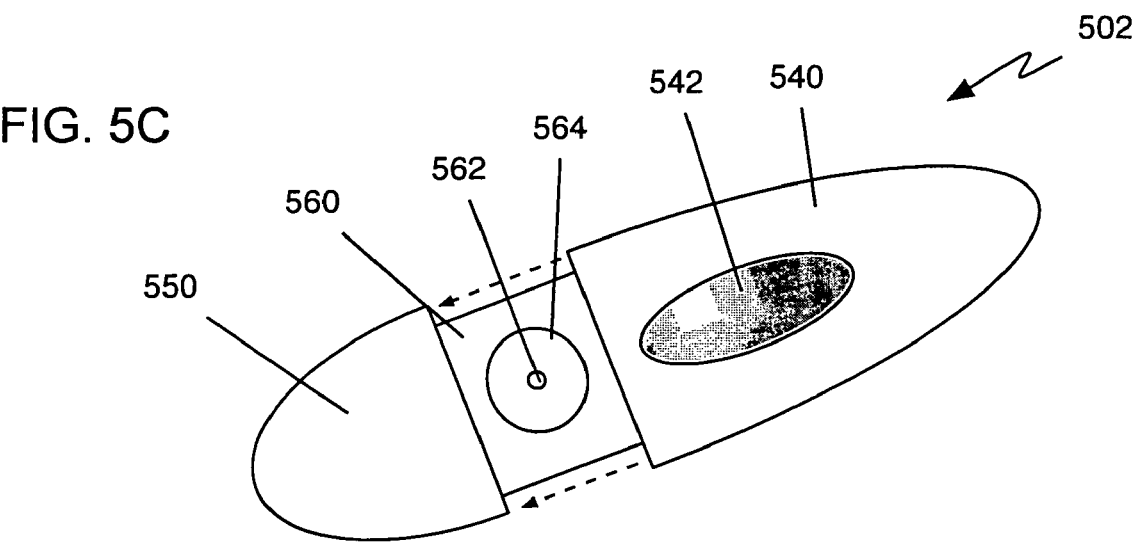

Referring now to FIG. 5C, an alternative liquid dispensing device 502 is shown. Unlike the embodiment of FIGS. 5A-B, dispensing device 502 includes a fixedly attached but movable cap 550. That is, rather than being completely removable, cap 550 may be slidably moved away from body 540 in order to expose mid piece 560 and aperture 562. Once exposed, liquid within body 540 may be forced through aperture 562 by squeezing bulb 542. Dispensing device 502 is particularly well suited for the dispensation of eyedrops and saline solutions. Once cap 550 is slidably moved to expose mid piece 560 and aperture 562, cap 550 may be balanced or steadied on the bridge of a user's nose as the eyedrops or saline solution is dispensed into the user's eye. Such an arrangement significantly improves the accuracy of dispensation, as compared to known dispensing devices, which do not permit a user to so balance or steady the device. Mid piece 560 may further comprise a ring 564 around aperture 562, useful in aiding a user's aim of the aperture 562 over his or her eye.

Figure 5D:
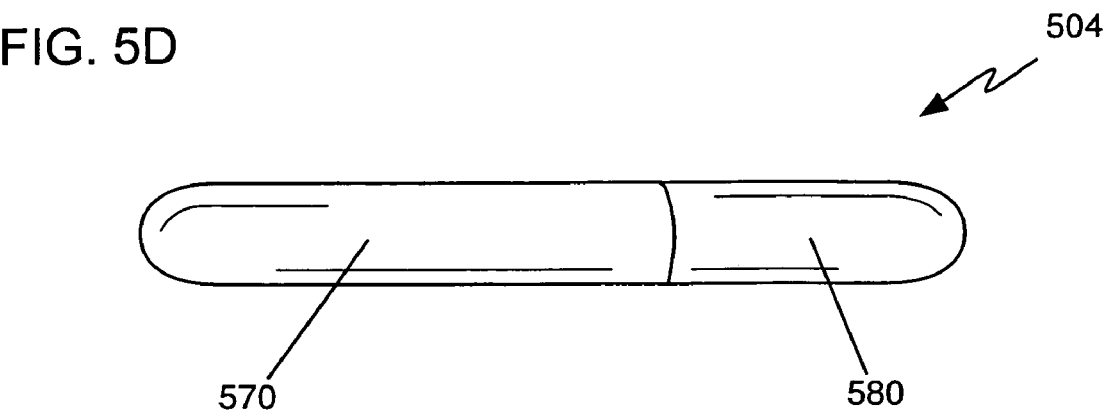
Figure 5E:
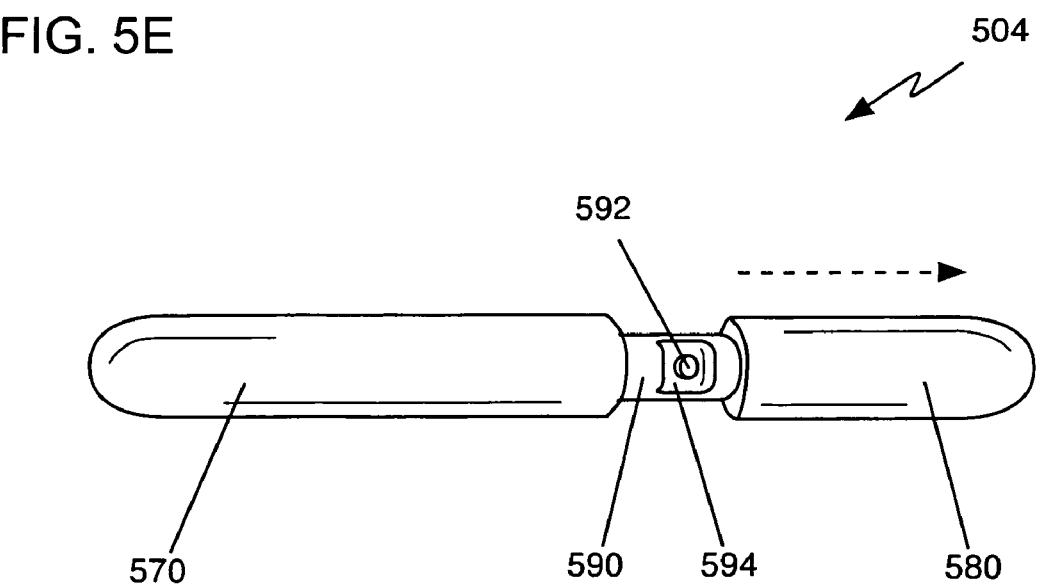

FIGS. 5D-E show yet another alternative embodiment of a liquid dispensing device 504 according to the invention. Dispensing device 504 has an elongate, tube-like shape comprising a reservoir/bulb 570 and handle 580. In FIG. 5D, dispensing device 504 is shown in its closed position, wherein handle 580 and reservoir/bulb 570 abut. In FIG. 5E, dispensing device 504 is shown in its open position, wherein handle 580 is extended away from reservoir/bulb 570 to expose midpiece 590. As in the embodiments in FIGS. 5A-C, midpiece 590 includes an aperture 592. In order to permit handle 580 to slide over midpiece 590, aperture 592 is disposed within a recess 594 in midpiece 590. In its open position, a user may dispense contents of reservoir/bulb 570 through aperture 592 by squeezing reservoir/bulb 570.

As above in FIG. 4C, one or more dispensing devices 500, 502, 504 of FIGS. 5A-E may be stored within a product container 100, such as that of FIGS. 1A-C. So storing dispensing devices 500, 502, 504 permits their storage and transport within a housing adapted to secure one or more product containers, as will be described in detail below.

Figure 6A:
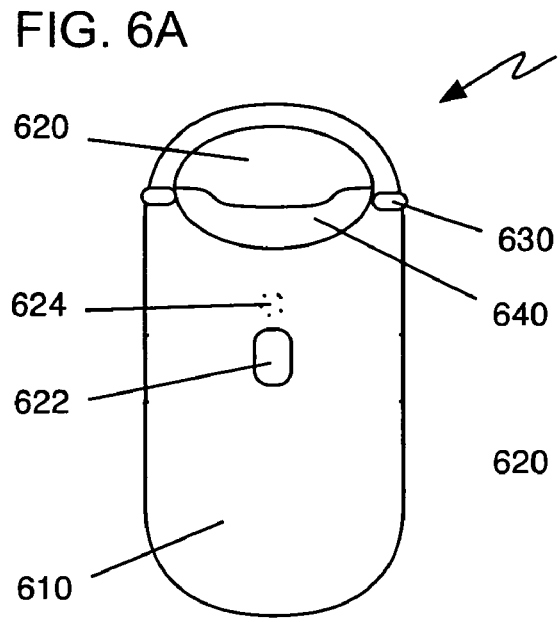
FIGS. 6A-C show an illustrative product container according to the invention for storing and dispensing a liquid as a spray.
Figure 6B:
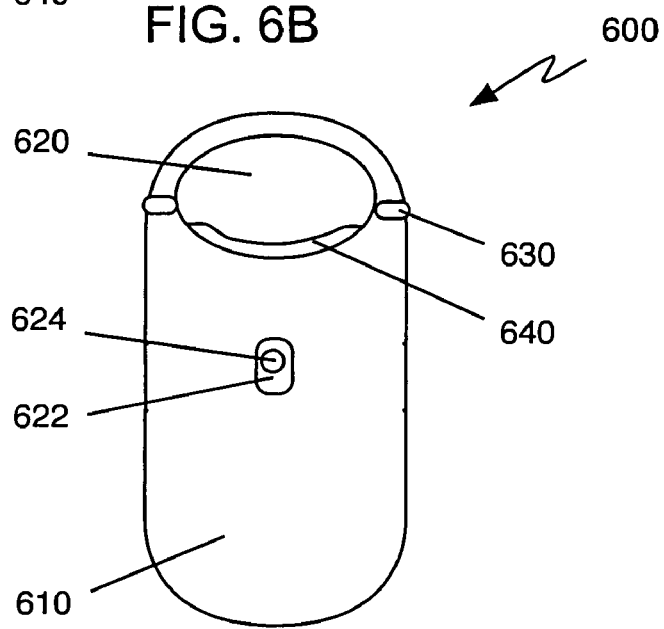
Figure 6C:
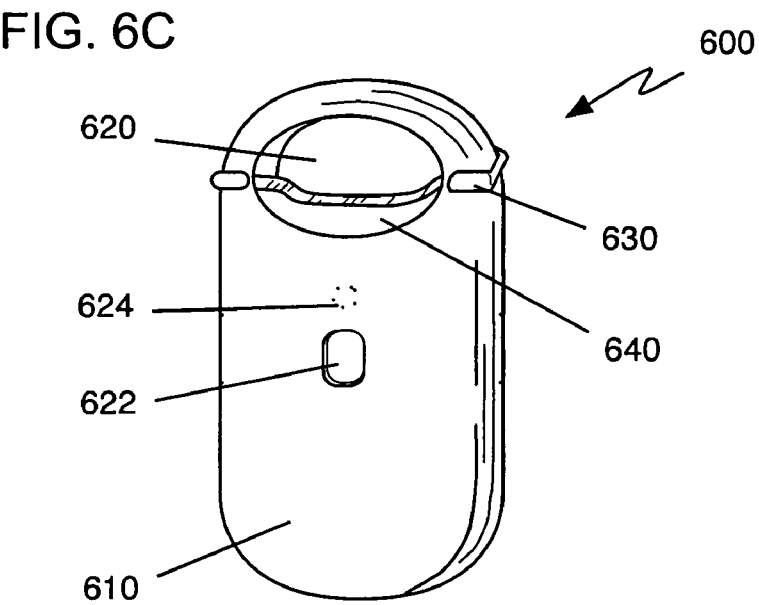

FIGS. 6A-C show a liquid dispensing device 600 for storing and dispensing a personal healthcare product in the form of a stream or mist. Dispensing device 600 includes a body 610 including a port 622, an opening 620 through which a user may place a finger or thumb, a plunger 640, and an aperture 624. The detailed mechanism of dispensation of dispensing device 600 is described in U.S. Patent Application Publication No. 20060032867, filed 2 Jun. 2005, which is hereby incorporated by reference. Briefly, FIG. 6A shows dispensing device 600 in its inactive state. Plunger 640 is in its raised position and aperture 624 (shown in phantom) is disposed above port 622. In such a state, liquid is not dispensed from device 600. In FIG. 6B, dispensing device 600 is shown in its active state. Plunger 640 is in its depressed position and aperture 624 is lowered to a position within port 622, allowing liquid within body 610 to be dispensed through aperture 624. FIG. 6C provides a partial side view of dispensing device 600 in its inactive state.

Unlike the devices described in U.S. Patent Application Publication No. 20060032867, dispensing device 600 includes attachment features 630 analogous to those of product container 100 (FIGS. 1A-C). As such, as will be described in detail below, dispensing device 600 may be stored and transported within a housing adapted to secure one or more product containers or dispensing devices.

Figure 7A:
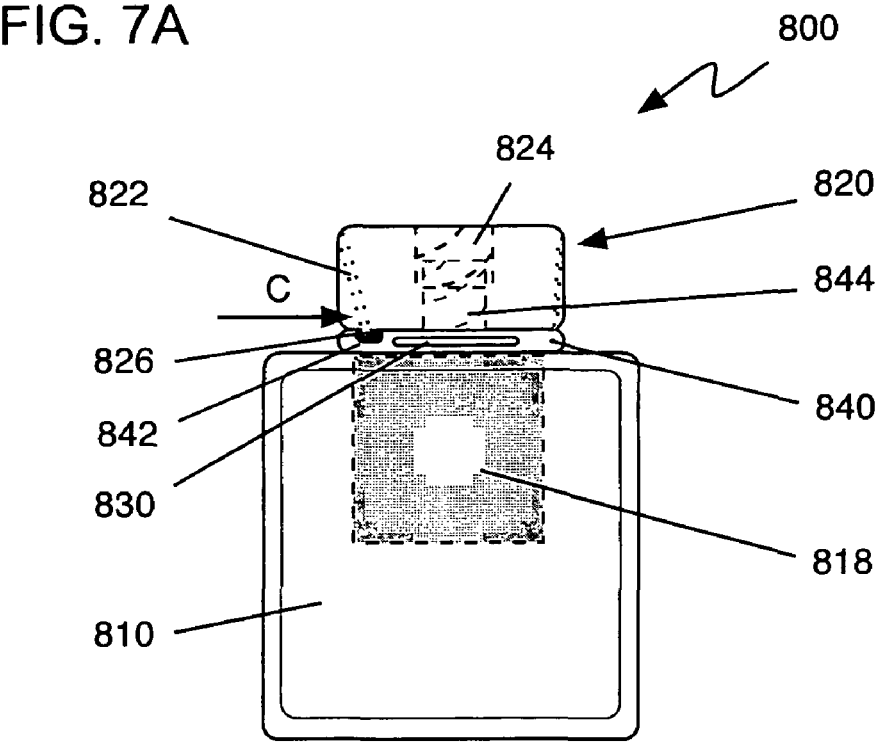
FIGS. 7A-D show a dispensing mechanism according to the invention.
Figure 7B:
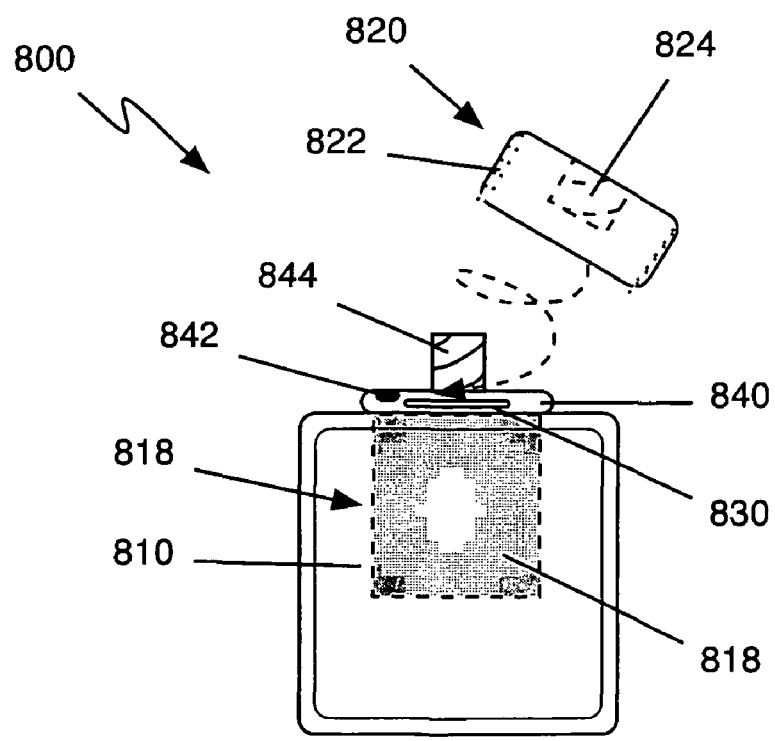
Figure 7C:
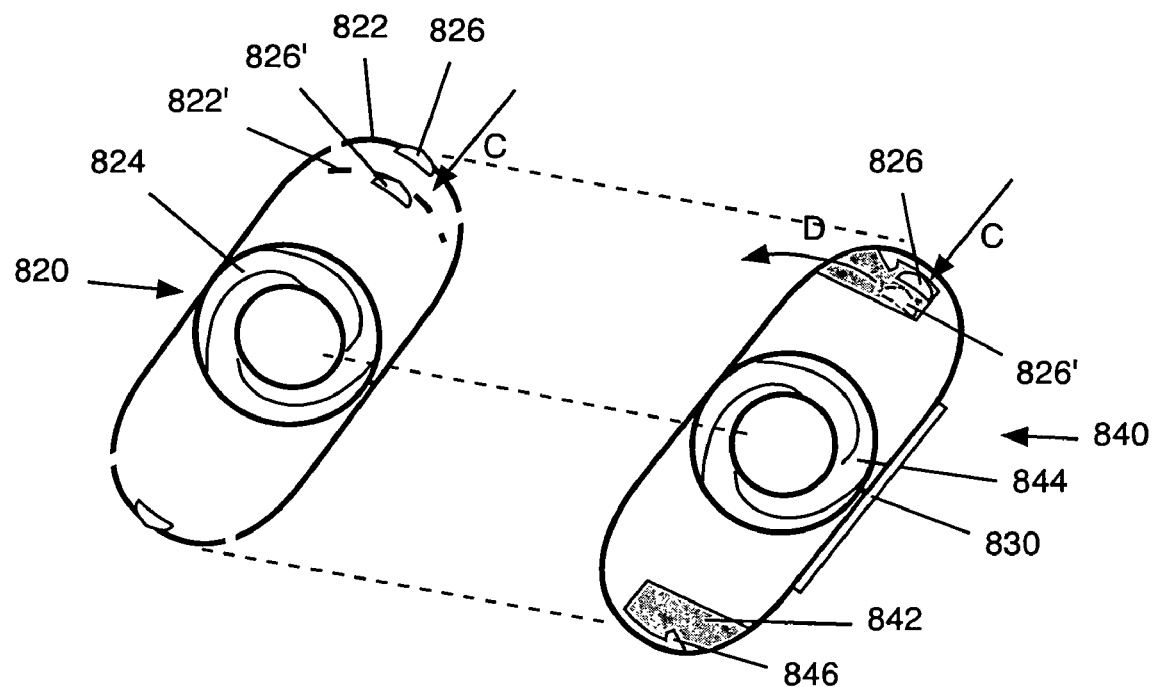

Referring now to FIGS. 7A-C, a child-resistant dispensing mechanism 800 according to the invention is shown. As will be described below, such a child-resistant dispensing mechanism may be included in a product container (e.g., 100 in FIGS. 1A-C), in the case that access to a healthcare product should be restricted, due, for example, to its toxicity.

In FIGS. 7A-D, a child-resistant dispensing mechanism 800 is shown comprising a cap member 820 and a base member 840. In FIGS. 7A-B, dispensing mechanism 800 is shown on a product container body 810 such as that in FIGS. 3A-B (i.e., a flexible body), although dispensing mechanism 800 may be used with any product container having any body type. As will be explained in greater detail below, in the case that body 810 comprises a flexible material, an interior rib 818 of base member 840 extends into body 810, thereby preventing a collapse of body 810 and ensuring that the contents of body 810 can be dispensed. Preferably, dispensing mechanism 800 includes an attachment feature 830, permitting the storage and transport of the product container to which it is attached within a housing adapted to secure one or more product containers or dispensing devices.

As shown in FIGS. 7A-C, cap member 820 includes a threaded female feature 824 adapted to accept a corresponding threaded male feature 844 in base member 840. Alternatively, cap member 820 may include a threaded male member and base member 840 may include a threaded female member. Other mechanisms for connecting cap member 820 and base member 840 and prevent loss of the container's contents will be recognized by one skilled in the art.

Cap member 820 includes at least one deflectable member 822. Deflectable member 822 is connected to cap member 820 along a single edge (i.e., adjacent a top surface of cap member 820). As such, deflected portions of deflectable member 822 move into an interior area of cap member 820. That is, as force is applied to deflectable member 822 along path C (FIGS. 7A, 7C), deflectable member 822 moves inward into cap member 820, with portions of deflectable member 822 further from its point of attachment to cap member 820 moving further into cap member 820 than portions of deflectable member 822 closer to its point of attachment.

Together, cap member 820 and base-member 840 provide a child-resistant mechanism. As can be seen in FIGS. 7A and 7C, a free end 826 of deflectable member 822 extends below a bottom edge of cap member 820 and into a slot 842 of base member 840. As such, in its undeflected state, deflectable member 822 is retained within slot 842, preventing the unthreading of cap member 820 from base member 840. However, upon the application of a force to deflectable member 822 (e.g., along path C), deflectable member 822, and specifically free end 826, may be removed from slot 842 upon the unthreading of cap member 820 from base member 840.

FIG. 7C shows the child-resistant features of cap member 820 and base member 840 in greater detail. In its undeflected state, deflectable member 822, including free end 826, resides along a periphery of cap member 820. However, upon the application of force along path C, deflectable member 822 and its free end 826 move inward to positions 822' and 826', respectively, within cap member 820.

Still referring to FIG. 7C, slot 842 of base member 840 is adapted to restrict movement of cap member 820 in the case that deflectable member 822 is in its undeflected state and to permit movement (i.e., unthreading) of cap member 820 in the case that deflectable member 822 is in its deflected state (i.e., 822'). More specifically, in the case that deflectable member 822 is in its undeflected state, free end 826 is substantially held within slot 842 by notch 846. However, upon the application of force along path C, deflected free end 826' is no longer restricted by notch 846 and cap member 820 may be unthreaded from base member 840 upon the application of a rotational force along path D.

Figure 7D:
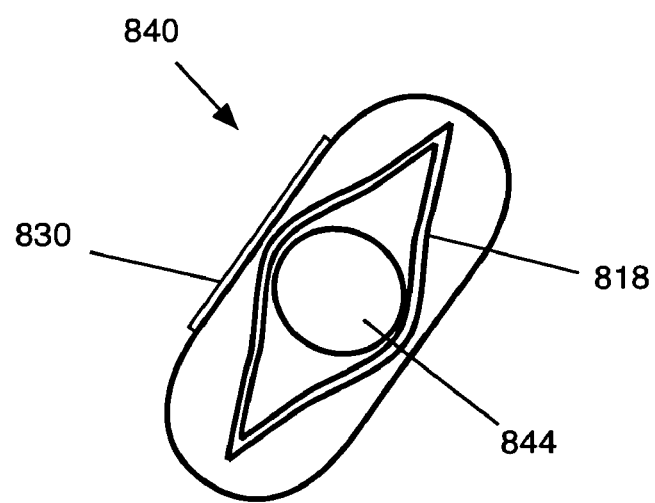

FIG. 7D shows an underside of base member 840 and, more particularly, the interior rib 818 of base member 840 described above. As depicted, interior rib 818 has a roughly diamond-like cross-sectional shape, although other shapes may be used. Interior rib 818 substantially surrounds an underside of threaded male feature 844, through which a product may be dispensed. As noted above, in the case that body 810 comprises a flexible material, interior rib 818 prevents collapse of body 810 (i.e., the contact of large areas of opposing inner surfaces of body 810), which may impede the dispensation of a product from body 810. In a preferred embodiment, at least a portion of an interior surface of body 810 is adhered to a surface of interior rib 818 using, for example, an adhesive.

Figure 8A:
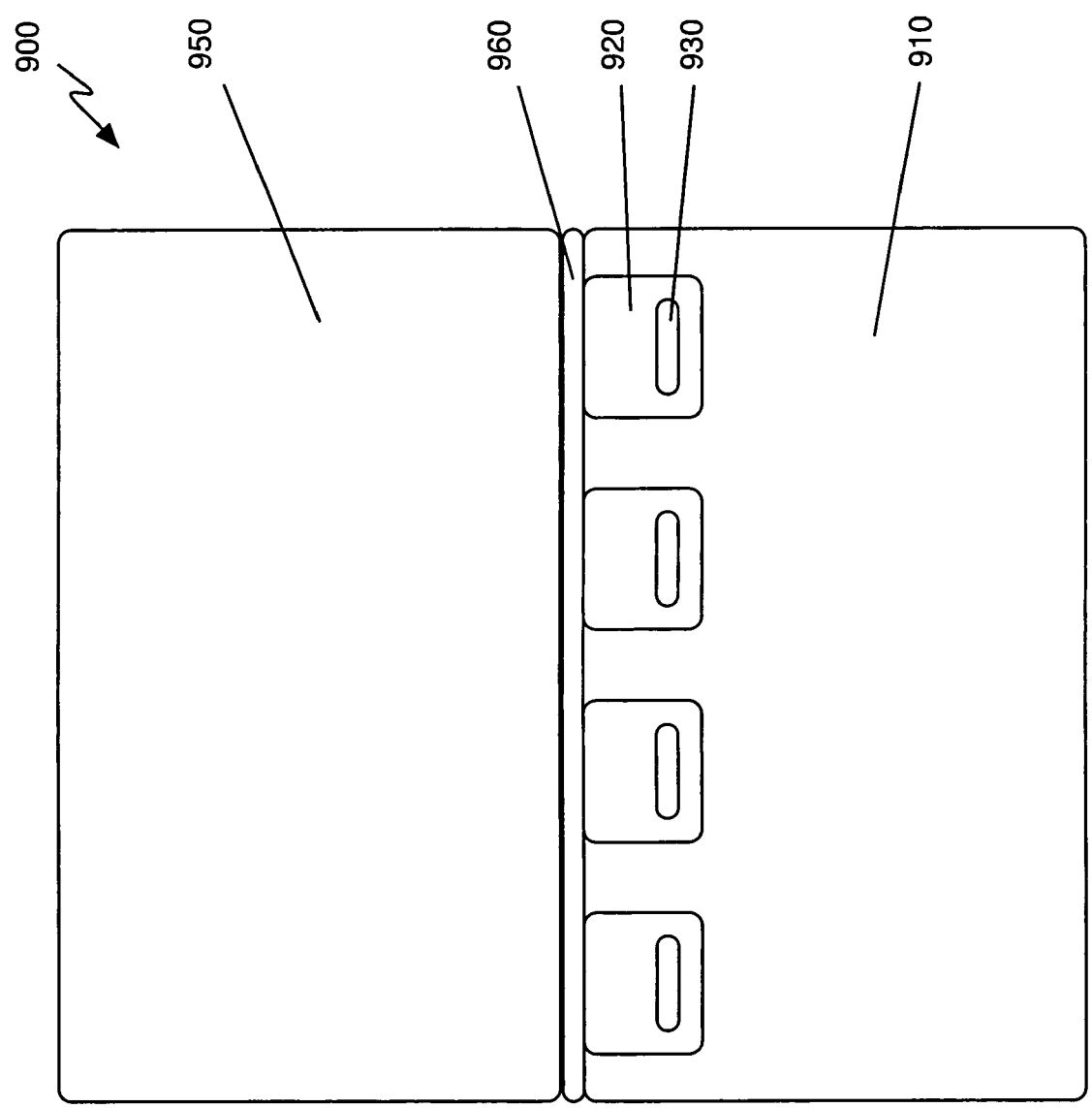

FIGS. 8A-D show a housing 900 for substantially securing one or more product containers according to the invention. In FIG. 8A, a housing 900 according to an embodiment of the present invention comprises a base 910, a lid 950, a hinge 960 between base 910 and lid 950, and a plurality of tabs 920 for securing product containers. As shown, each tab 920 includes a mating feature 930 adapted to be compatible with an attachment feature (e.g., 130 of FIG. 1A), such that a pairing of mating feature 930 and attachment feature 130 substantially secures a product container (e.g., 100 of FIG. 1A) to housing 900.

As noted above with respect to FIG. 1A, attachment feature 130 may include any number of devices or mechanisms, as will be recognized by one having skill in the art. As shown in FIGS. 8A-D, and as will be described in greater detail below, mating feature 930 comprises an indentation or groove adapted to be compatible with the ridge or protrusion of attachment feature 130.

Referring now to FIG. 8B, housing 900 is shown with a plurality of product containers 100A, 100B, 200, each of the plurality in various stages of insertion into and substantial securing to housing 900. Product container 100A has been introduced substantially within the space defined by base 910. Product container 100B has been inserted further into housing 900, such that a portion of its dispensing portion 120 (FIG. 1A) resides beneath tab 920B. However, the attachment feature 130 (FIG. 1A) of product container 100B has not yet been secured to mating feature 930B of tab 920B. Product container 200 is shown fully inserted into housing 900, such that mating feature 930C of tab 920C has been secured to attachment feature 230A (FIG. 2). In the case that product container 200 includes a second attachment feature 230B (FIG. 2), it has similarly been secured to mating feature 930D of tab 920D.

Once each desired product container (e.g., 100A, 100B, 200) has been fully inserted into and secured to housing 900, lid 950 may be rotated about hinge 960, moving housing 900 to a closed position. Lid 950, base 910, or any other portion of housing 900 may further include a device or mechanism for substantially securing lid 950 to base 910, as will be recognized by one having skill in the art. Such an embodiment is particularly useful for storing and transporting personal healthcare products during travel.

It should be noted, however, that other embodiments of housing 900 are, of course, possible. For example, housing 900 need not include lid 950 or hinge 960. Such an embodiment, comprising base 910 and one or more tabs 930A-D, may be advantageous for storing personal healthcare products that are accessed frequently.

Figure 8C:
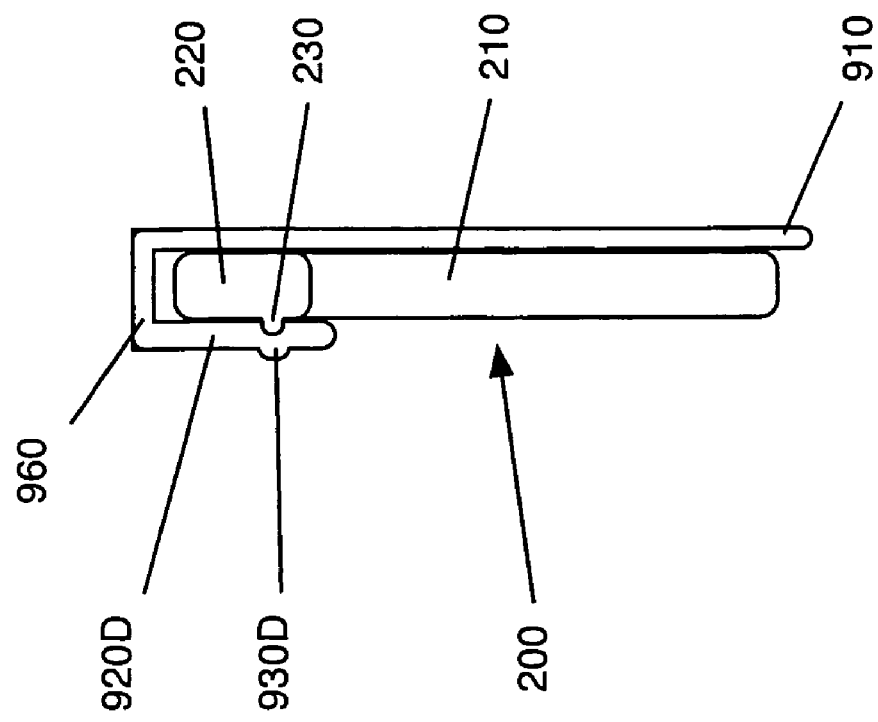
Figure 8D:
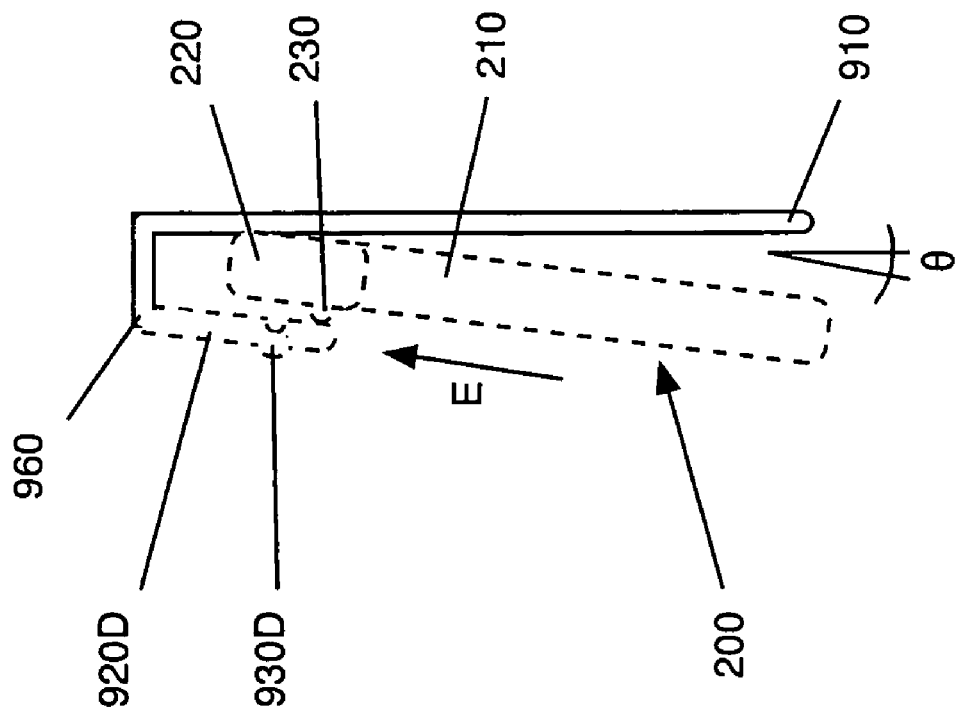

FIGS. 8C-D show cross-sectional views of product container 200 during and following, respectively, securing to tab 920D. In FIG. 8C, product container 200 is shown at a slight angle (theta) with respect to base 910. Upon insertion of product container 200 along path E and beneath tab 920D, the distal portion of tab 920D is deflected slightly away from base 910 in order to accommodate product container 200. In a preferred embodiment, a depth of product container (e.g., a depth of dispensing portion 220) is slightly greater than the space between tab 920D (in its non-deflected, resting position) and base 910. Such an arrangement provides an interference between product container 200, tab 920D, and base 910.

In FIG. 8D, product container 200 has been fully inserted between tab 920D and base 910, such that attachment feature 230 resides adjacent mating feature 930D. The connection of attachment feature 230 and mating feature 930D, in addition to the interference between product container 200, tab 920D, and base 910 described above, substantially secures product container between tab 920D and base 910. As shown in FIG. 8D, the distal end of tab 920D has fully or substantially returned to its non-deflected position.

FIGS. 9A-G show yet another embodiment of the invention comprising a case 1000 into which one or more housing 900 may be fixedly or non-fixedly attached. Preferably, housings 900 is non-fixedly attached. Case 1000 is a box-like structure comprising a base 1010, a base wall 1012 substantially perpendicular to base 1010, a lid 1050, and a lid wall 1052 substantially perpendicular to lid 1050. Case 1000 may include any number of additional features to provide added functionality and/or convenience. For example, an interior surface of base 1010 may include a flexible member 1014, such as a sheet of fabric, plastic, elastic, etc., thereby forming a pocket between flexible member 1014 and base 1010. This may be useful, for example, for storing a user's prescriptions, instructions for use of a personal healthcare product, etc.

Figure 9A:
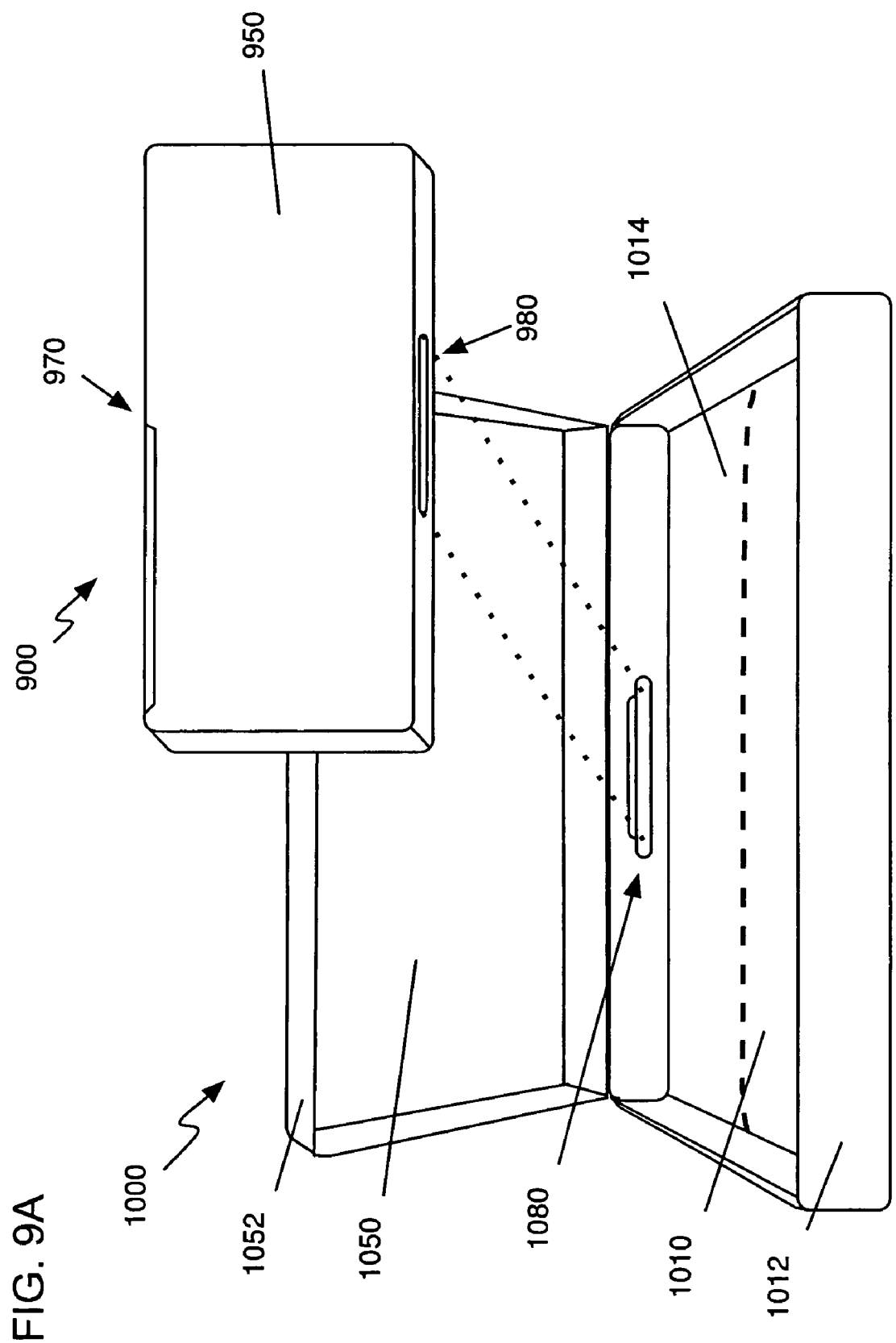

As shown in FIG. 9A, housing 900 is similar to that of FIGS. 8A-B. However, housing 900 further comprises a slot 980 for securing housing 900 to an interior portion of case 1000. Case 1000 includes a corresponding bar 1080 adapted to fit within slot 980, thereby substantially securing housing 900 to case 1000.

Figure 9D:
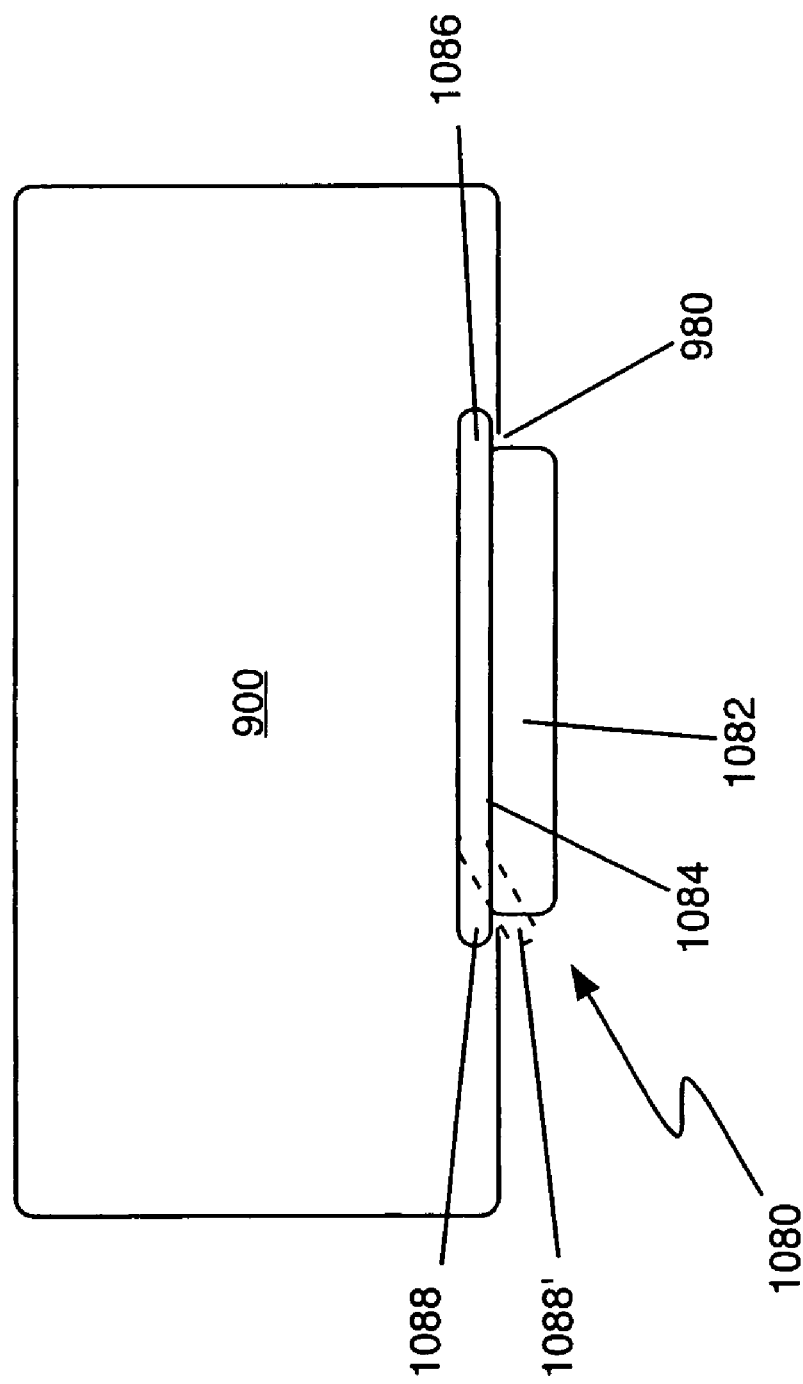

FIGS. 9B-D show more detailed views of the securing of housing 900 to case 1000. FIG. 9B shows housing 900 and bar 1080 in cross section. Bar 1080 comprises a rod 1084 having a substantially circular cross section and a fin 1082 to which rod 1084 is attached. Rod 1084 and at least a portion of fin 1082 are adapted to fit within slot 980 of housing 900.

FIG. 9C shows a side view of housing 900 and bar 1080. As can be seen, rod 1084 has a width B that is preferably slightly wider than a width A of slot 980, such that an interference is formed between rod 1084 and slot 980 during the insertion of bar 1080 into slot 980. That is, rod 1084 includes ends 1086, 1088 extending beyond fin 1082, which are adapted to contact a surface of housing 900 adjacent slot 980 upon the insertion of bar 1080 into slot 980. As such, rod 1084 is preferably at least partially comprised of a flexible material such that ends 1086, 1088 may deflect as bar 1080 is inserted into slot 980. FIG. 9D shows bar 1080 following its insertion into slot 980 of housing 900. As can be seen, end 1088 is deflected (1088') during insertion, such that, upon insertion, rod 1084 is held within housing 900, thereby substantially and non-fixedly securing housing 900 to bar 1080.

Figure 9F:
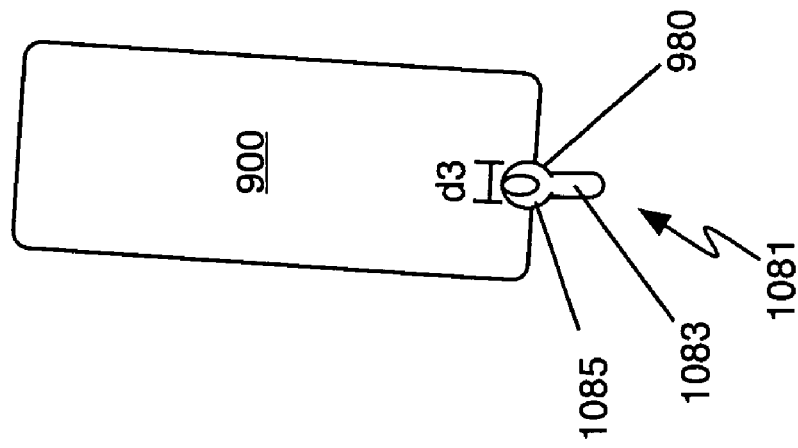
Figure 9E:
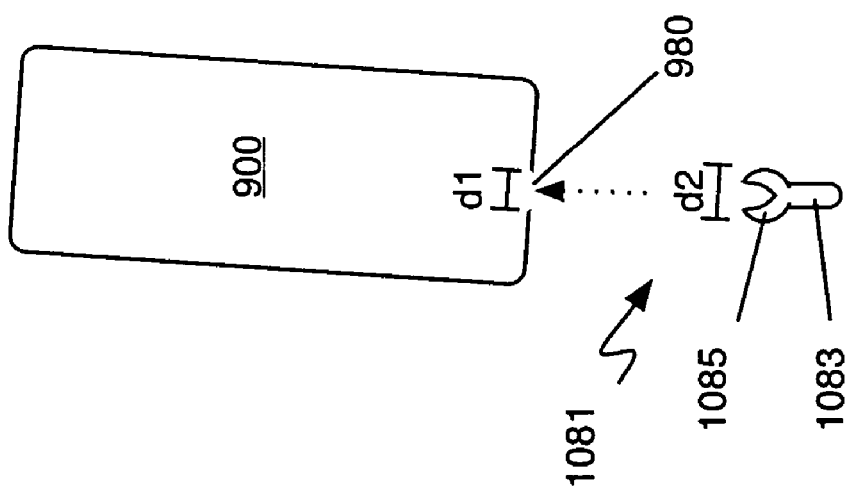

FIGS. 9E-F show an alternative mechanism for attaching a bar 1081 (and therefore a case, not shown) to a housing 900. As shown in FIGS. 9E-F, rod 1085 is partially split in a radial direction, such that, in its relaxed position in FIG. 9E, a diameter d2 is greater than a diameter d1 of slot 980. However, upon insertion of rod 1085 into slot 980, rod 1085 takes on the compressed position of FIG. 9F, wherein rod 1085 has a diameter d3 less than or equal to diameter d1 of slot 980. Once inserted within housing 900, rod 1085 may return to its relaxed position, wherein its diameter d2 is greater than the diameter d1 of slot 980, thereby substantially preventing the removal of bar 1081 from housing 900. To facilitate the change in rod 1085 between its relaxed position and compressed position, rod 1085 is preferably at least partially comprised of a flexible material.

Figure 9G:
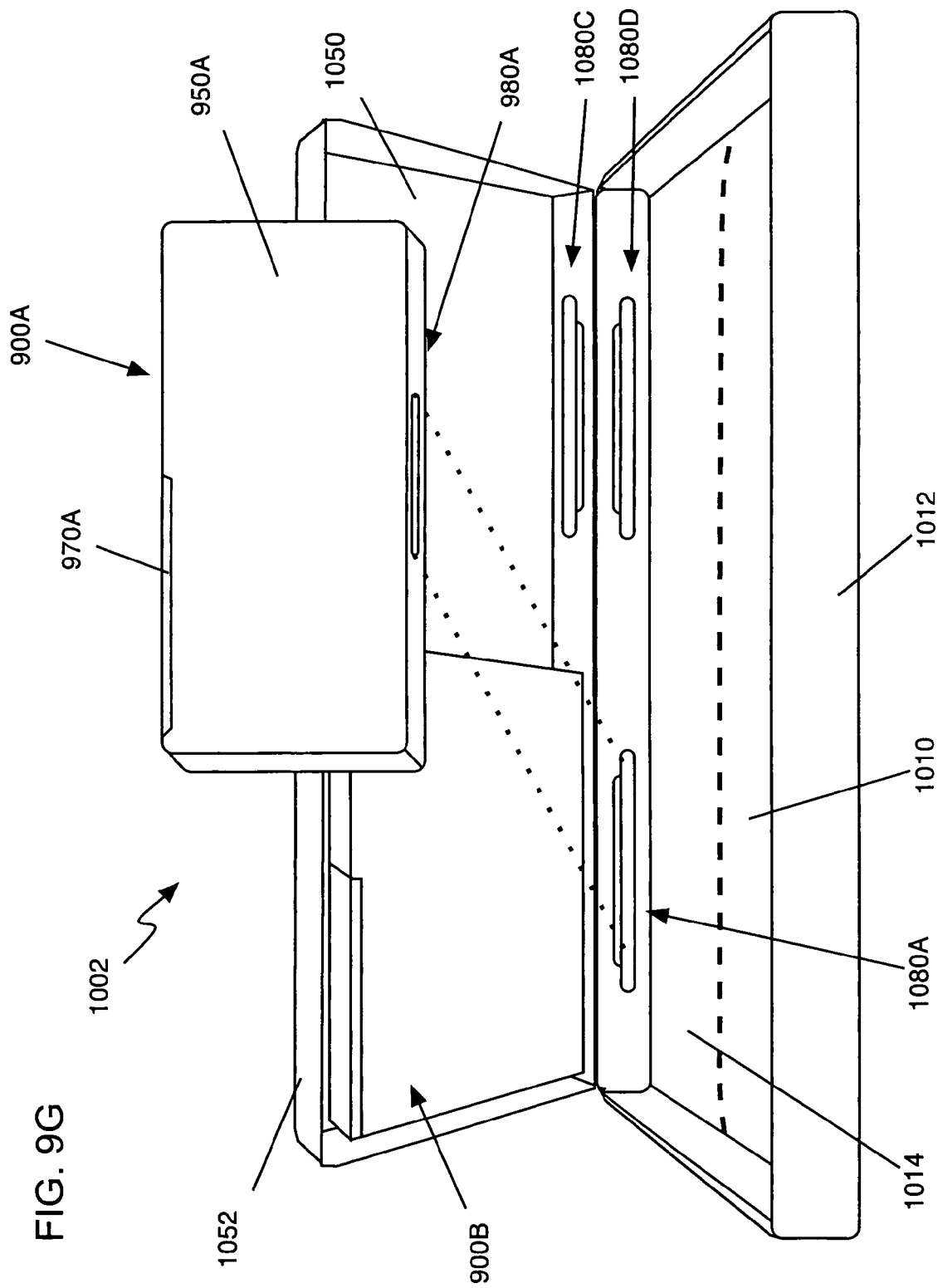

FIG. 9G shows an alternative embodiment of a case 1002 according to the invention. Case 1002 includes a plurality of bars 1080A, 1080B (obscured), 1080C, 1080D for securing a plurality (i.e., up to four) of housings 900A, 900B. As shown in FIG. 9E a pair of bars is located along an inner surface of each of base wall 1012 and lid wall 1052. Any number of alternative arrangements is also possible, as will be recognized by one skilled in the art.

Cases 1000, 1002 according to the invention may be adapted to contain any number of housings 900. Similarly, as will be recognized by one having skill in the art, housings 900 contained within case 1000 may be of varying shapes and sizes, permitting the removal and replacement of one housing 900 with another. For example, a smaller housing (not shown) suitable for storage of a one- or two-day supply of personal healthcare products may be replaced with a larger housing (e.g., 900) suitable for storage of a week's supply of personal healthcare products. Accordingly, housings 900 may be provided to a consumer fully stocked with preselected personal healthcare products, such that a consumer need only purchase one or more housings 900 rather than individual product containers.

Turning now to FIGS. 10A-B, a bag 1100 is shown adapted for use with a case 1000, 1002, such as those in FIGS. 9A and 9E. Bag 1100 comprises a flexible body 1120 and a rigid frame 1110. Frame 1110 includes a slot 1180 similar to that shown in housing 900 (FIGS. 9A-E). As such, bag 1100 may be substantially and non-fixedly secured to bar 1080 and stored within a case 1000, 1002 in a manner similar to the securing and storage of housing 900 described above. Body 1120 may be fixedly or non-fixedly secured to frame 1110 by any number of methods, including, for example, an adhesive, hooks and loops, and a thermal joint.

Bag 1100 allows a user to store and transport personal healthcare products or other materials that are either not provided in product containers adapted for use with a housing or are not suitable for use in such product containers. Examples of such products include, for example, cosmetics and bottled prescription medications. In the case that a user has a need or a desire to store and/or transport such products, they may be placed within body 1120 of bag 1100, and bag 1100 secured within a case 1000, 1002 according to the invention. Such a use of bag 1100 may be in place of or in addition to the use of a housing 900 according to the invention. Preferably, body 1120 includes a closure 1170 to prevent the loss of products stored within it. As will be recognized by one skilled in the art, any number of closure devices may be employed, including, for example, a zipper, a snap, a clasp, hooks and loops, a button, and an adhesive. Preferably, closure 1170 includes a zipper 1172.

Figure 11A:
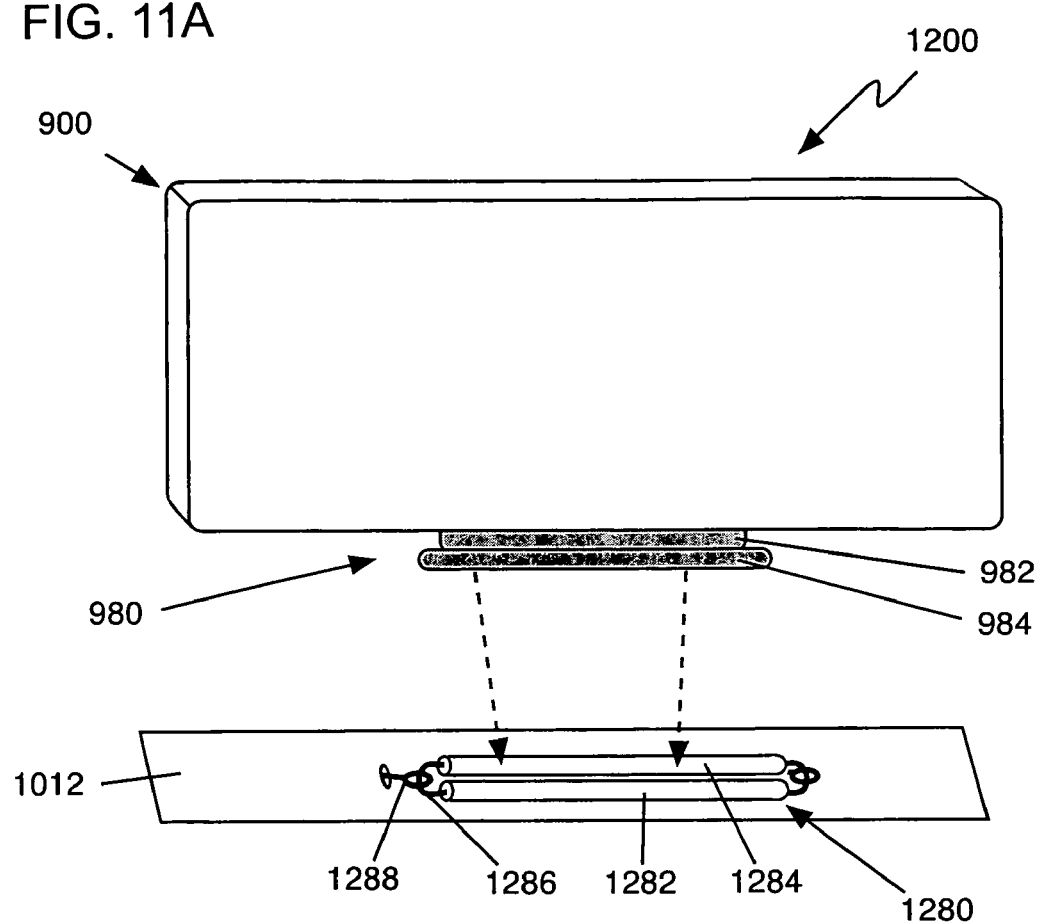
FIGS. 11A-D show alternative attachment mechanisms for cases and product container housings according to the invention.
Figure 11B:
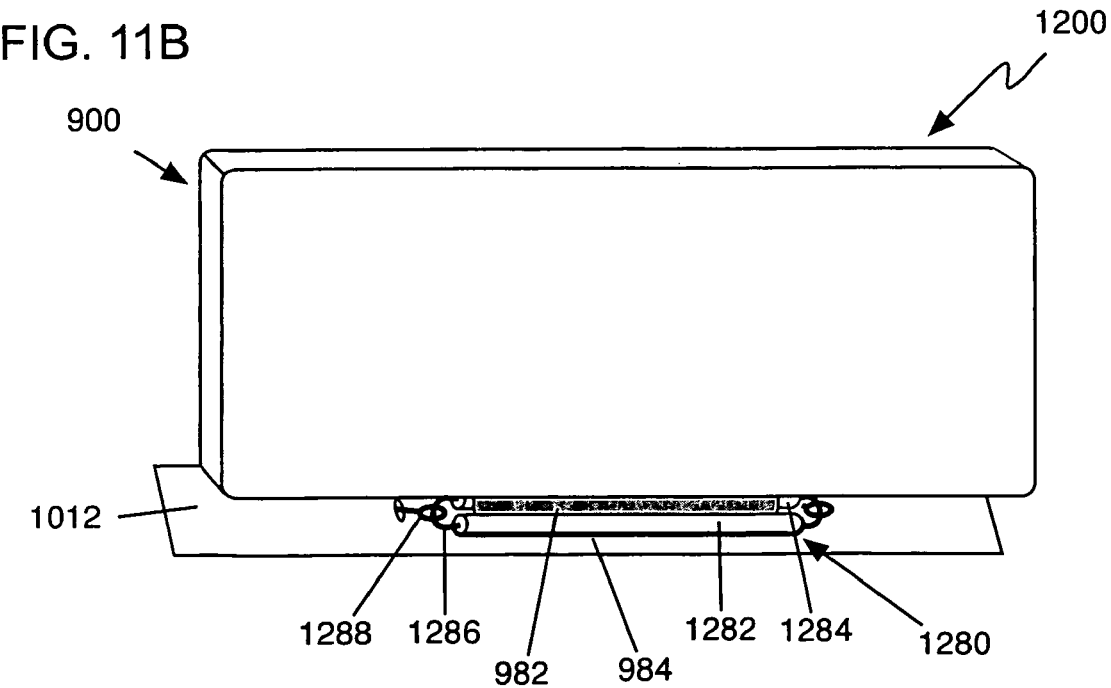

FIGS. 11A-D shown alternative devices for securing a housing 900 or bag 1100 to a case 1000, 1002 according to the invention. In FIGS. 11A-B, bar 980 is located on housing 900 rather than within case 1000 (FIGS. 9A, 9E). An inner surface of base wall 1012, for example, includes a pair of parallel rods 1282, 1284, between which rod 984 of bar 980 may be placed. Parallel rods 1282, 1284 are spaced such that an amount of force must be applied in order to pass rod 984 between them, as shown in FIG. 11B. However, as shown in FIG. 9B, because rod 984 has a width greater than that of fin 982, once rod 984 is passed between parallel rods 1282, 1284, a similar force will be required to dislodge bar 980. Bar 980 is shaded to help distinguish it from parallel rods 1282, 1284 in FIG. 11B.

As shown in FIGS. 11A-B, parallel rods 1282, 1284 are maintained in a parallel orientation by one or more loops 1286 running through each parallel rod 1282, 1284 and secured to base wall 1012 by, for example, one or more rings 1288. Other mechanisms are also possible, as will be known by one skilled in the art.

Figure 11C:
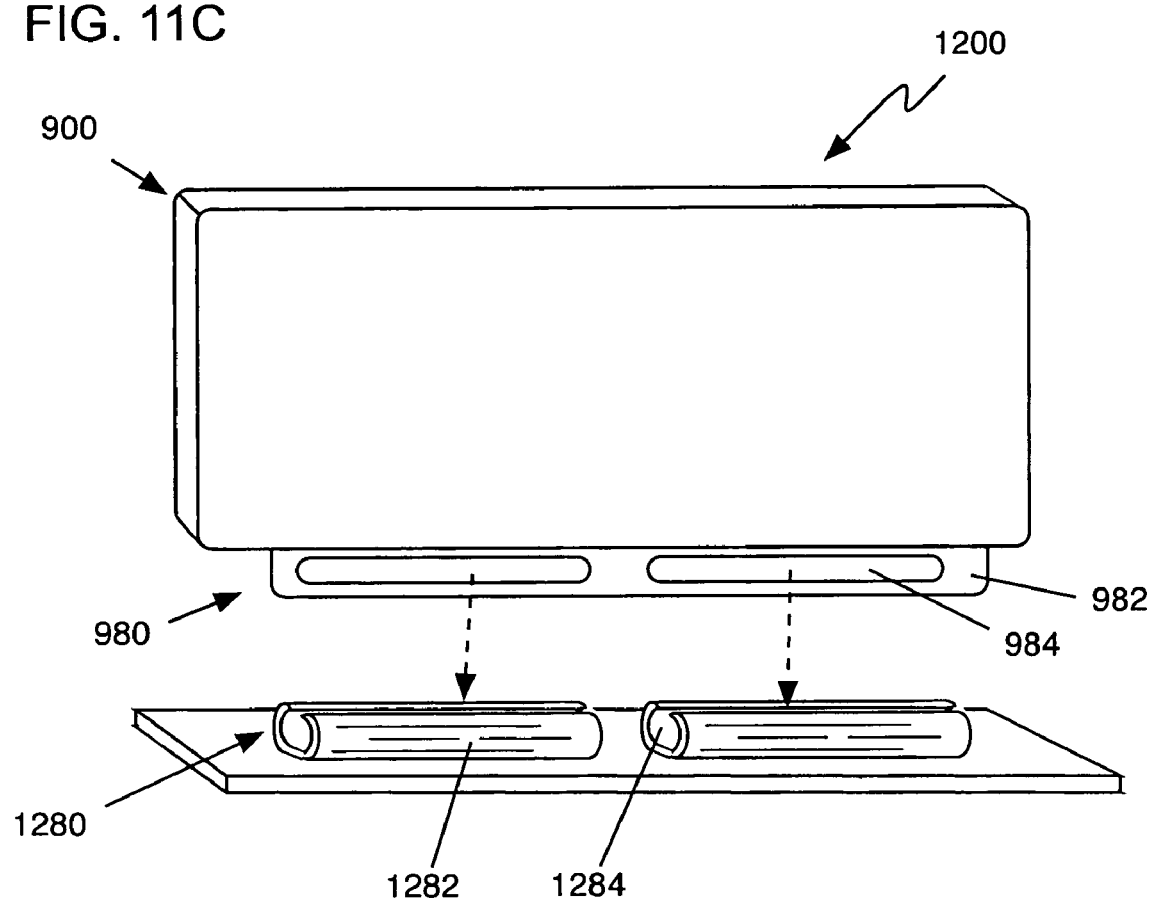
Figure 11D:
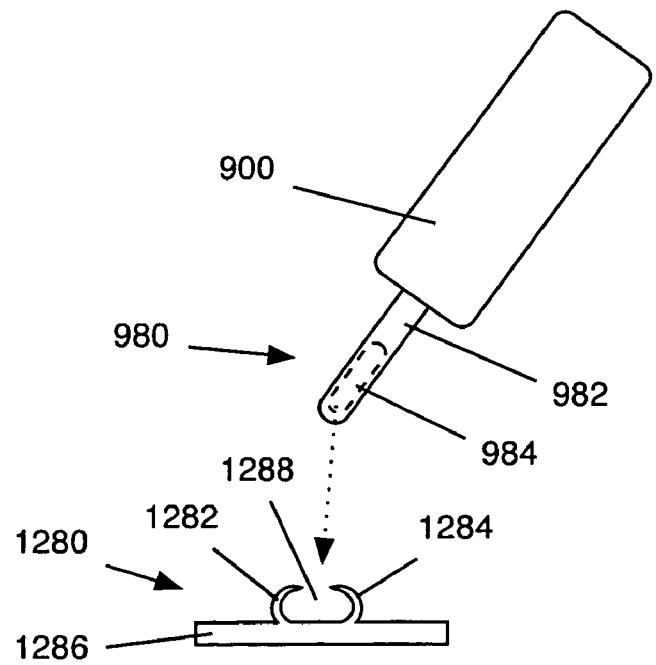

In FIGS. 11C-D, another alternative device for securing housing 900 or bag 1100 to a case 1000, 1002 is shown. Housing 900 includes a rail 980 having one or more openings 984 formed in a fin 982. A case according to the invention may contain one or more corresponding channels 1280 having a base 1286 and a pair of crescent-shaped members 1282, 1284. A void 1288 is formed between crescent-shaped members 1282, 1284 into which rail 980 may be placed. More specifically, fin 982 of rail 980 may be located within void 1288, while the free ends of crescent-shaped members 1282, 1284 pass partially into opening 984. Such an arrangement permits rail 980 (and therefore housing 900) to pivot about rail 980, much like a page in a book. Any number of similar attachment devices may be similarly employed, as will be recognized by one skilled in the art.

The devices described above make it possible to merchandise personal healthcare products in a single area of a merchandiser's establishment by providing a plurality of personal healthcare products, each being packaged in a product container such as those described above and adapted to be secured to a housing. Optionally, one or more such personal healthcare products may be provided within or in conjunction with a housing and/or a case, such that a purchaser need not have previously purchased either a housing or a case in order to make use of the product containers.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

What is claimed is:

1. A child-resistant dispensing mechanism comprising:
a cap portion including at least one deflectable member; and
a base portion including at least one groove adapted to receive at least a portion of said at least one deflectable member;
wherein:
said cap portion is positioned above and adapted for releasable coupling with said base portion;
said at least a portion of said at least one deflectable member, in a non-deflected state, is located within said at least one groove and within said base portion when said cap portion is coupled with said base portion;
said base portion has an elongated cross-section with opposing longer sides and opposing shorter sides;
said at least one groove opens to the exterior of said base portion;
said groove has a notch confining said at least a portion of said at least one deflectable member in a section of said groove to inhibit movement of said cap portion and substantially to prevent said cap portion from being removed from said base portion; and
said at least a portion of said at least one deflectable member, in a deflected state, may be moved past said notch and be removed from said at least one groove to move to a position not above said base portion as said cap portion is being removed from said base portion yet still coupled with said base portion.

2. The mechanism of claim 1, wherein said base portion is adapted to be secured to a container.

3. The mechanism of claim 1, wherein:
said at least one groove includes a slot portion adapted to receive said at least a portion of said at least one deflectable member; and
said notch has an edge portion adapted to substantially secure said portion of said at least one deflectable member within said at least one groove.

4. The mechanism of claim 1, wherein said cap portion includes two deflectable members.

5. The mechanism of claim 1, wherein said cap portion has an elongated cross-section corresponding to said elongated cross-section of said base portion permitting said deflectable member, upon exiting said at least one groove, to no longer be positioned above said base portion.

6. The mechanism of claim 1, wherein said at least one deflectable member is moved inwardly of an outer periphery of said side walls of said cap portion and into a position within said cap portion when said at least one deflectable member is in said deflected state.

7. The mechanism of claim 1, wherein:
said at least one groove is formed between an outer groove wall along the periphery of said base portion and an inner groove wall spaced inwardly from said outer groove wall, and opens to a periphery of said base portion; and
said notch is provided along one of said outer groove wall and said inner groove wall extending inwardly into said at least one groove to block said at least a portion of said deflectable member from exiting said at least one groove.

8. A child-resistant dispensing mechanism comprising:
a cap portion having an elongated cross-section in a closed, undeflected rest position with opposing longer sides and opposing shorter sides, a deflectable member disposed on at least one of said opposing shorter sides, and a connecting feature;

a base portion having at least one groove each adapted to receive at least a portion of said deflectable member, and a connecting feature adapted for connecting with said connecting feature of said cap portion;

wherein:

said cap portion connecting feature and said base portion connecting feature have matching cross-sectional shapes in respective undeflected resting configurations;

said cap portion and said base portion are adapted for releasable coupling together upon mating of said cap portion connecting feature with said base portion connecting feature;

said groove is shaped to inhibit rotation of said cap portion by blocking movement of said deflectable member, thereby substantially preventing said cap portion from being removed from said base portion; and said at least a portion of said deflectable member is movable into a deflected state in which said at least a portion of said deflectable member is movable out of said groove.

9. The mechanism of claim 8, wherein:

said cap portion has a top surface; and said at least one deflectable member is connected to said cap portion along a single edge adjacent said top surface of said cap portion.

10. The mechanism of claim 9, wherein said at least one deflectable member is defined by a slit on either side thereof.

11. The mechanism of claim 8, wherein:

said at least one groove includes a slot defined by an outer groove wall along the periphery of said base portion and an inner groove wall spaced inwardly from said outer groove wall, and a notch extending from one of said outer groove wall and said inner groove wall inwardly into said slot;

said slot is adapted to receive said at least a portion of said at least one deflectable member;

said notch has an edge portion adapted to block said at least a portion of said at least one deflectable member from exiting said at least one slot when said at least a portion of said at least one deflectable member is in an undeflected state; and in a deflected state, said at least a portion of said at least one deflectable member is movable past said notch and out of said slot.

12. The mechanism of claim 8, wherein said cap portion connecting feature and said base portion connecting feature are threaded features with substantially circular cross-sections for threaded engagement with each other.

13. A child-resistant dispensing mechanism comprising:

a cap portion having an elongated cross-section and a downwardly extending side wall with an outer periphery; and a base portion adapted for releasable coupling with said cap portion;

wherein:

said side wall of said cap portion has opposing longer sides and opposing shorter sides;

a break in said side wall of said cap portion between each of said opposing longer sides and said opposing shorter sides forms a deflectable member disposed on each of said opposing shorter sides and residing along and in line with said outer periphery of said cap portion to form said opposing shorter side walls;

said base portion has two grooves each adapted to receive at least a portion of a respective one of said deflectable members;

said grooves are shaped to inhibit rotation of said cap portion by blocking movement of said deflectable members, thereby substantially preventing said cap portion from being removed from said base portion; and said at least a portion of said deflectable members are movable into a deflected state in which said at least a portion of said deflectable members are movable out of said grooves.

14. The mechanism of claim 13, wherein said deflectable members are moved inwardly of said outer periphery of said side walls of said cap portion when said at least a portion of said deflectable members are in said deflected state.

15. The mechanism of claim 13, wherein:

said cap portion has a top surface; and said at least one deflectable member is connected to said cap portion along a single edge adjacent said top surface of said cap portion.

16. A child-resistant dispensing mechanism comprising:

a cap portion having a top surface, a bottom edge opposite said top surface, and side walls with an outer periphery extending around the entire circumference of said cap portion; and a base portion having an upwardly-facing top surface, at least one groove extending downwardly into said base portion top surface, and an outer periphery extending around the entire circumference of said base portion and aligned with and matching said cap portion outer periphery;

wherein:

said cap portion and said base portion are adapted for releasable coupling together;

said cap portion has at least one deflectable member residing along and in line with said outer periphery of said side walls of said cap portion to form at least a portion of said opposing side walls of said cap portion and having a free end extending downwardly below said bottom edge of said cap portion;

when said cap portion is coupled to said base portion, said bottom edge of said cap portion is immediately above and adjacent to said top surface of said base portion, and said free end of said at least one deflectable member extends downwardly into said at least one groove in said base portion and below said top surface of said base portion to be hidden from view below said top surface of said base portion; and said groove is shaped to inhibit rotation of said cap portion by blocking movement of said free end of said at least one deflectable member, thereby substantially preventing said cap portion from being removed from said base portion.

17. The mechanism of claim 16, wherein the only portion of said cap portion within said at least one groove is said free end of said at least one deflectable member.

18. The mechanism of claim 16, wherein:

said at least one groove includes a slot defined by an outer groove wall along the periphery of said base portion and an inner groove wall spaced inwardly from said outer groove wall, and a notch extending from one of said outer groove wall and said inner groove wall inwardly into said slot;

said slot is adapted to receive said free end of said at least one deflectable member;

said notch has an edge portion adapted to block said free end of said at least one deflectable member from exiting said slot when said free end of said at least one deflectable member is in an undeflected state; and in a deflected state, said free end of said at least one deflectable member is movable past said notch and out of said slot.

19. The mechanism of claim 16, wherein
said at least one deflectable member is connected to said cap portion along a single edge adjacent said top surface of said cap portion.

20. The mechanism of claim 16, wherein said at least one deflectable member is moved inwardly of said outer periphery of said side walls of said cap portion and into a position within said cap portion when said at least one deflectable member is in said deflected state.

21. A method of using an elongated tube-like shaped liquid dispensing device having a longitudinal axis, an elongated liquid-containing reservoir extending along said longitudinal axis, a mid portion including an aperture transverse to said longitudinal axis, and an elongated cover portion coupled to said liquid dispensing device and extending along said longitudinal axis and adapted to alternately cover and reveal said aperture, said method comprising:
   slidably moving said cover portion along said longitudinal axis without removing said cover portion from said liquid dispensing device to reveal said aperture and to further elongate said elongated liquid dispensing device;
   balancing said cover portion on a user's nose to position said aperture above the user's eye to facilitate dispensing of liquid into the user's eye;
   squeezing a portion of said liquid dispensing device to dispense liquid from said reservoir through said aperture and into the user's eye.

22. The method of claim 21, wherein said liquid dispensing device includes one of the following: a depression in a surface of said liquid-containing portion; a raised area on a surface of said liquid-containing portion; and a marking on a surface of said liquid-containing portion.

23. The method of claim 21, wherein said liquid-containing portion is adapted to contain at least one of: an eyedrop solution and a saline solution.

24. The method of claim 23, wherein said aperture is disposed within a recess in said mid portion to permit said cover portion to slide over said mid portion to cover said aperture.

25. The method of claim 23, wherein said liquid dispensing device further comprises a ring member around said aperture, said method further comprising positioning said ring member above the user's eye to aid a user in directing dispensation of liquid from said aperture into the user's eye.

26. A child-resistant dispensing mechanism comprising:
   a cap portion having, in a closed, undeflected rest postion, an elongated cross-section with opposing longer sides and opposing shorter sides, and a downwardly extending side wall with an outer periphery; and
   a base portion having an elongated cross-section with opposing longer sides and opposing shorter sides corresponding to said elongated cross-section of said cap portion;
wherein:
   said cap portion is adapted for releasable coupling with said base portion;
   said elongated cross-section of said cap portion matches said elongated cross-section of said base portion when said cap portion is closed on said base portion in an undeflected resting position;
   said cap portion has at least one deflectable member along one of said shorter sides and said base portion has at least one groove adapted to receive at least a portion of said least one deflectable member;
   said at least one groove is shaped to inhibit rotation of said cap portion by blocking movement of said at least one deflectable member, thereby substantially preventing said cap portion from being removed from said base portion;
   said at least a portion of said at least one deflectable member is movable into a deflected state in which said at least a portion of said at least one deflectable member is movable out of said at least one groove.

27. The mechanism of claim 26, wherein said at least one groove provides a positive lock preventing rotation of said cap portion with respect to said base portion when said at least a portion of said at least one deflectable member is within said groove.

* * * * *